(12) United States Patent
Bonadio et al.

(10) Patent No.: US 9,351,759 B2
(45) Date of Patent: May 31, 2016

(54) INSTRUMENT ACCESS DEVICE

(75) Inventors: Frank Bonadio, Bray (IE); Trevor Vaugh, Birr (IE); Ronan B. McManus, Bray (IE); Shane J. MacNally, Delgany (IE); Michael Mulhall, Oranmore (IE)

(73) Assignee: Atropos Limited, County Wicklow (IE)

( * ) Notice: Subject to any disclaimer, the term of this patent is extended or adjusted under 35 U.S.C. 154(b) by 428 days.

(21) Appl. No.: 13/445,737

(22) Filed: Apr. 12, 2012

(65) Prior Publication Data

US 2013/0041231 A1    Feb. 14, 2013

Related U.S. Application Data

(63) Continuation of application No. 12/885,011, filed on Sep. 17, 2010, now abandoned, which is a continuation-in-part of application No. 12/694,888, filed on Jan. 27, 2010, now Pat. No. 8,657,740, which (Continued)

(51) Int. Cl.
*A61B 17/02* (2006.01)
*A61B 17/34* (2006.01)
*A61B 17/00* (2006.01)

(52) U.S. Cl.
CPC .......... *A61B 17/3423* (2013.01); *A61B 17/3462* (2013.01); *A61B 17/3431* (2013.01); *A61B 17/3468* (2013.01); *A61B 17/3474* (2013.01); *A61B 17/3498* (2013.01); *A61B 2017/00477* (2013.01); *A61B 2017/3445* (2013.01); *A61B 2017/3449* (2013.01); *A61B 2017/3466* (2013.01); *A61B 2017/3484* (2013.01); *A61B 2017/3492* (2013.01)

(58) Field of Classification Search
CPC ........... A61B 17/3423; A61B 17/3462; A61B 17/02; A61B 17/0206; A61B 2017/0212; A61B 17/0218; A61B 2017/0225; A61B 2017/3419; A61B 2017/3425; A61B 17/3431; A61B 2017/3445; A61B 2017/3447; A61B 2017/3449
USPC ........................... 606/201–246; 600/201-246
See application file for complete search history.

(56) References Cited

U.S. PATENT DOCUMENTS 1,157,202 A    10/1915    McLeland
1,598,284 A    8/1926    Kinney (Continued)

FOREIGN PATENT DOCUMENTS

DE    37 39 532    12/1988
DE    37 37 121    5/1989

(Continued)

OTHER PUBLICATIONS

Kagaya, "Laparoscopic cholecystectomy via two ports, using the 'Twin-Port' system", J. Hepatobiliary Pancreat Surg (2001) 8:76-80.

(Continued)

*Primary Examiner* — Jerry Cumberledge
(74) *Attorney, Agent, or Firm* — Bookoff McAndrews, PLLC

(57) ABSTRACT

An instrument access device 1 comprises a proximal member 25 for location externally of an opening into a body cavity. A first connector 20 extends between the proximal member 25 and a first instrument receiver 2. A second connector 21 extends between the proximal member and a second instrument receiver 3. Instrument seals can be housed in relatively rigid housings for added strength.

17 Claims, 26 Drawing Sheets

Related U.S. Application Data is a continuation-in-part of application No. 12/133,827, filed on Jun. 5, 2008, now Pat. No. 8,187,178.

(60) Provisional application No. 60/924,918, filed on Jun. 5, 2007, provisional application No. 60/935,625, filed on Aug. 22, 2007, provisional application No. 60/996,760, filed on Dec. 4, 2007, provisional application No. 61/243,295, filed on Sep. 17, 2009, provisional application No. 61/147,625, filed on Jan. 27, 2009, provisional application No. 61/147,613, filed on Jan. 27, 2009.

(56) References Cited

U.S. PATENT DOCUMENTS

| | | |
|---|---|---|
| 1,810,466 A | 6/1931 | Deutsch |
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,592,198 A | 7/1971 | Evans |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Macintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 3,998,217 A | 12/1976 | Trumbull et al. |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,112,932 A * | 9/1978 | Chiulli ............ 604/264 |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumuto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,002,557 A | 3/1991 | Hasson |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima |
| 5,125,897 A | 6/1992 | Quinn et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Strouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,261,883 A | 11/1993 | Hood et al. |
| 5,263,922 A | 11/1993 | Sova et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |

(56) References Cited

U.S. PATENT DOCUMENTS

| | | | |
|---|---|---|---|
| 5,308,336 | A | 5/1994 | Hart et al. |
| 5,309,896 | A | 5/1994 | Moll et al. |
| 5,316,541 | A | 5/1994 | Fischer |
| 5,320,611 | A | 6/1994 | Bonutti |
| 5,330,437 | A | 7/1994 | Durman |
| 5,330,497 | A | 7/1994 | Freitas |
| 5,334,143 | A | 8/1994 | Carroll |
| 5,336,192 | A | 8/1994 | Palestrant |
| 5,342,315 | A | 8/1994 | Rowe et al. |
| 5,342,385 | A | 8/1994 | Norelli et al. |
| 5,350,364 | A | 9/1994 | Stephens et al. |
| 5,364,345 | A | 11/1994 | Lowery et al. |
| 5,366,478 | A | 11/1994 | Brinkerhoff et al. |
| 5,368,545 | A | 11/1994 | Schaller et al. |
| 5,383,861 | A | 1/1995 | Hempel |
| 5,385,553 | A | 1/1995 | Hart et al. |
| 5,391,153 | A | 2/1995 | Haber et al. |
| 5,391,156 | A | 2/1995 | Hildwein et al. |
| 5,395,367 | A | 3/1995 | Wilk |
| 5,403,264 | A | 4/1995 | Wohlers |
| 5,407,433 | A | 4/1995 | Loomas |
| 5,423,848 | A | 6/1995 | Washizuka et al. |
| 5,429,609 | A | 7/1995 | Yoon |
| 5,431,676 | A | 7/1995 | Durbal |
| 5,443,452 | A | 8/1995 | Hart et al. |
| 5,456,284 | A | 10/1995 | Ryan |
| 5,476,475 | A | 12/1995 | Gadberry |
| 5,480,410 | A | 1/1996 | Cuschieri et al. |
| 5,496,280 | A | 3/1996 | Vandenbroeck |
| 5,503,112 | A | 4/1996 | Luhman |
| 5,514,109 | A | 5/1996 | Mollenauer et al. |
| 5,514,133 | A | 5/1996 | Golub et al. |
| 5,520,632 | A | 5/1996 | Leveen |
| 5,522,791 | A | 6/1996 | Leyva |
| 5,522,824 | A | 6/1996 | Ashby |
| 5,524,644 | A | 6/1996 | Crook |
| 5,526,536 | A | 6/1996 | Cartmill |
| 5,545,179 | A | 8/1996 | Williamson, IV |
| 5,562,632 | A | 10/1996 | Davila |
| 5,562,688 | A | 10/1996 | Riza |
| 5,577,993 | A | 11/1996 | Zhu et al. |
| 5,582,577 | A | 12/1996 | Lund et al. |
| 5,584,850 | A | 12/1996 | Hart et al. |
| 5,601,579 | A | 2/1997 | Semertzides |
| 5,620,415 | A | 4/1997 | Lucey |
| 5,632,979 | A | 5/1997 | Goldberg |
| 5,634,911 | A | 6/1997 | Hermann et al. |
| 5,634,936 | A | 6/1997 | Linden |
| 5,634,937 | A | 6/1997 | Mollenauer et al. |
| 5,636,645 | A | 6/1997 | Ou |
| 5,640,977 | A | 6/1997 | Leahy et al. |
| 5,649,550 | A | 7/1997 | Crook |
| 5,653,705 | A | 8/1997 | de la Torre et al. |
| 5,657,963 | A | 8/1997 | Hinchliffe |
| 5,658,272 | A | 8/1997 | Hasson |
| 5,658,306 | A | 8/1997 | Kieturakis |
| 5,672,168 | A | 9/1997 | de la Torre et al. |
| 5,685,854 | A | 11/1997 | Green |
| 5,707,703 | A | 1/1998 | Rothrum et al. |
| 5,709,664 | A | 1/1998 | Vandenbroeck |
| 5,720,730 | A | 2/1998 | Blake, III |
| 5,738,628 | A | 4/1998 | Sierocuk et al. |
| 5,741,234 | A | 4/1998 | Aboul-Hosn |
| 5,741,298 | A | 4/1998 | MacLeod |
| 5,743,884 | A | 4/1998 | Hasson et al. |
| 5,749,882 | A | 5/1998 | Hart et al. |
| 5,755,660 | A | 5/1998 | Tyagi |
| 5,769,783 | A | 6/1998 | Fowler |
| 5,769,794 | A | 6/1998 | Conlan et al. |
| 5,782,812 | A | 7/1998 | Hart et al. |
| 5,795,290 | A | 8/1998 | Bridges |
| 5,803,919 | A | 9/1998 | Hart et al. |
| 5,803,921 | A | 9/1998 | Bonadio |
| 5,807,350 | A | 9/1998 | Diaz |
| 5,810,721 | A | 9/1998 | Mueller et al. |
| 5,813,409 | A | 9/1998 | Leahy et al. |
| 5,814,026 | A | 9/1998 | Yoon |
| 5,817,062 | A | 10/1998 | Flom |
| 5,820,555 | A | 10/1998 | Mueller |
| 5,832,925 | A | 11/1998 | Rothrum |
| 5,848,992 | A | 12/1998 | Hart et al. |
| 5,853,395 | A | 12/1998 | Crook et al. |
| 5,865,728 | A | 2/1999 | Moll et al. |
| 5,871,474 | A | 2/1999 | Hermann et al. |
| 5,882,344 | A | 3/1999 | Strouder |
| 5,899,208 | A | 5/1999 | Bonadio |
| 5,904,703 | A | 5/1999 | Gilson |
| 5,906,577 | A * | 5/1999 | Beane et al. ................ 600/207 |
| 5,916,232 | A | 6/1999 | Hart |
| 5,947,922 | A | 9/1999 | MacLeod |
| 5,951,467 | A | 9/1999 | Picha et al. |
| 5,957,913 | A | 9/1999 | de la Torre et al. |
| 5,964,781 | A | 10/1999 | Mollenauer et al. |
| 5,993,485 | A | 11/1999 | Beckers |
| 5,994,450 | A | 11/1999 | Pearce |
| 5,997,515 | A | 12/1999 | de la Torre et al. |
| 6,024,736 | A | 2/2000 | de la Torre et al. |
| 6,025,067 | A | 2/2000 | Fay |
| 6,033,426 | A | 3/2000 | Kaji |
| 6,033,428 | A | 3/2000 | Sardella |
| 6,036,685 | A | 3/2000 | Mueller |
| 6,042,573 | A | 3/2000 | Lucey |
| 6,144,700 | A | 3/2000 | Mueller |
| 6,048,309 | A | 4/2000 | Flom et al. |
| 6,059,816 | A | 5/2000 | Moenning |
| 6,077,288 | A | 6/2000 | Shimomura et al. |
| 6,099,506 | A | 8/2000 | Macoviak et al. |
| 6,110,154 | A | 8/2000 | Shimomura et al. |
| 6,123,689 | A | 9/2000 | To |
| 6,142,935 | A | 11/2000 | Flom et al. |
| 6,142,936 | A | 11/2000 | Beane et al. |
| 6,149,642 | A | 11/2000 | Gerhart et al. |
| 6,150,608 | A | 11/2000 | Wambeke |
| 6,159,182 | A | 12/2000 | Davis |
| 6,162,172 | A | 12/2000 | Cosgrove et al. |
| 6,162,196 | A | 12/2000 | Hart et al. |
| 6,162,206 | A | 12/2000 | Bindokas |
| 6,163,949 | A | 12/2000 | Neuenschwander |
| 6,164,279 | A | 12/2000 | Tweedle |
| 6,171,282 | B1 | 1/2001 | Ragsdale |
| 6,183,486 | B1 | 2/2001 | Snow et al. |
| 6,238,373 | B1 | 5/2001 | de la Torre et al. |
| 6,254,533 | B1 | 7/2001 | Fadem et al. |
| 6,254,534 | B1 | 7/2001 | Butler et al. |
| 6,258,065 | B1 | 7/2001 | Dennis et al. |
| 6,315,770 | B1 | 11/2001 | de la Torre et al. |
| 6,319,246 | B1 | 11/2001 | de la Torre et al. |
| 6,322,541 | B2 | 11/2001 | West |
| 6,328,730 | B1 * | 12/2001 | Harkrider, Jr. ................ 604/523 |
| 6,346,074 | B1 | 2/2002 | Roth |
| 6,382,211 | B1 | 5/2002 | Crook |
| 6,420,475 | B1 | 7/2002 | Chen |
| 6,440,063 | B1 | 8/2002 | Beane |
| 6,450,983 | B1 | 9/2002 | Rambo |
| 6,454,783 | B1 | 9/2002 | Piskun |
| 6,458,543 | B1 | 10/2002 | Gold et al. |
| 6,464,686 | B1 | 10/2002 | O'Hara et al. |
| 6,485,435 | B1 | 11/2002 | Bakal |
| 6,485,467 | B1 | 11/2002 | Crook et al. |
| 6,488,620 | B1 | 12/2002 | Segermark et al. |
| 6,533,734 | B1 | 3/2003 | Corley, III et al. |
| 6,551,270 | B1 | 4/2003 | Bimbo et al. |
| 6,554,793 | B1 | 4/2003 | Pauker |
| 6,569,119 | B1 | 5/2003 | Haberland et al. |
| 6,578,577 | B2 | 6/2003 | Bonadio et al. |
| 6,582,364 | B2 | 6/2003 | Butler et al. |
| 6,589,167 | B1 | 7/2003 | Shimonmura |
| 6,589,211 | B1 | 7/2003 | MacLeod |
| 6,607,504 | B2 | 8/2003 | Haarala |
| 6,613,952 | B2 | 9/2003 | Rambo |
| 6,623,426 | B2 | 9/2003 | Bonadio et al. |
| 6,706,050 | B1 | 3/2004 | Giannadakis |
| 6,714,298 | B2 | 3/2004 | Ryer |
| 6,723,044 | B2 | 4/2004 | Pulford |

(56) References Cited

U.S. PATENT DOCUMENTS

| | | |
|---|---|---|
| 6,793,621 B2 | 9/2004 | Butler et al. |
| 6,796,940 B2 | 9/2004 | Bonadio et al. |
| 6,797,765 B2 | 9/2004 | Pearce |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,866,861 B1 | 3/2005 | Luhman |
| 6,884,253 B1 | 4/2005 | McFarlane |
| 6,902,541 B2 | 6/2005 | McNally et al. |
| 6,908,430 B2 | 6/2005 | Caldwell |
| 6,916,331 B2 | 7/2005 | Mollenauer et al. |
| 6,936,037 B2 | 8/2005 | Bubb |
| 6,939,296 B2 | 9/2005 | Ewers |
| 6,945,932 B1 | 9/2005 | Caldwell et al. |
| 6,958,037 B2 | 10/2005 | Ewers |
| 6,979,324 B2 | 12/2005 | Bybordi |
| 7,008,377 B2 | 3/2006 | Beane |
| 7,052,454 B2 | 5/2006 | Taylor |
| 7,081,089 B2 | 7/2006 | Bonadio et al. |
| 7,083,626 B2 | 8/2006 | Hart et al. |
| 7,112,185 B2 | 9/2006 | Hart et al. |
| 7,118,528 B1 | 10/2006 | Piskun |
| 7,153,319 B1 | 12/2006 | Haberland et al. |
| 7,195,590 B2 | 3/2007 | Butler et al. |
| 7,297,106 B2 | 11/2007 | Yamada et al. |
| 7,300,399 B2 | 11/2007 | Bonadio et al. |
| 7,344,547 B2 | 3/2008 | Piskun |
| 7,445,597 B2 | 11/2008 | Butler et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,749,415 B2 | 7/2010 | Brustad et al. |
| 7,753,901 B2 * | 7/2010 | Piskun et al. ............ 604/539 |
| 7,837,612 B2 | 11/2010 | Gill et al. |
| 7,867,164 B2 | 1/2011 | Butler et al. |
| 7,909,760 B2 | 3/2011 | Albrecht et al. |
| 7,998,068 B2 | 8/2011 | Bonadio et al. |
| 8,012,088 B2 | 9/2011 | Butler et al. |
| 8,021,296 B2 | 9/2011 | Bonadio et al. |
| 8,157,817 B2 | 4/2012 | Bonadio et al. |
| 8,187,178 B2 | 5/2012 | Bonadio et al. |
| 8,317,691 B2 | 11/2012 | Bonadio et al. |
| 8,343,047 B2 * | 1/2013 | Albrecht et al. ............ 600/206 |
| 8,375,955 B2 | 2/2013 | Desai et al. |
| 8,518,024 B2 | 8/2013 | Williams et al. |
| 8,657,740 B2 | 2/2014 | Bonadio et al. |
| 8,734,336 B2 | 5/2014 | Bonadio et al. |
| 8,876,708 B1 * | 11/2014 | Piskun et al. ............ 600/204 |
| 8,961,407 B2 * | 2/2015 | Piskun et al. ............ 600/204 |
| 2001/0037053 A1 | 11/2001 | Bonadio et al. |
| 2001/0039430 A1 | 11/2001 | Dubrul et al. |
| 2001/0047188 A1 | 11/2001 | Bonadio et al. |
| 2002/0002324 A1 | 1/2002 | Mcmanus |
| 2002/0010389 A1 | 1/2002 | Butler et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0028179 A1 | 2/2003 | Piskun |
| 2003/0078478 A1 | 4/2003 | Bonadio et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0068232 A1 | 4/2004 | Hart et al. |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0143158 A1 | 7/2004 | Hart et al. |
| 2004/0154624 A1 | 8/2004 | Bonadio et al. |
| 2004/0215063 A1 | 10/2004 | Bonadio et al. |
| 2004/0230161 A1 | 11/2004 | Zeiner |
| 2004/0249248 A1 | 12/2004 | Bonadio et al. |
| 2004/0260244 A1 | 12/2004 | Piechowicz et al. |
| 2005/0020884 A1 | 1/2005 | Heart et al. |
| 2005/0033246 A1 | 2/2005 | Ahlberg |
| 2005/0059865 A1 | 3/2005 | Kahle |
| 2005/0065475 A1 | 3/2005 | Hart et al. |
| 2005/0065543 A1 | 3/2005 | Kahle |
| 2005/0090713 A1 | 4/2005 | Gozales |
| 2005/0090716 A1 | 4/2005 | Bonadio et al. |
| 2005/0090717 A1 | 4/2005 | Bonadio et al. |
| 2005/0131349 A1 | 6/2005 | Albrecht |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0267419 A1 | 12/2005 | Smith |
| 2005/0277946 A1 | 12/2005 | Greenhalgh |
| 2005/0288558 A1 | 12/2005 | Ewers |
| 2005/0288634 A1 | 12/2005 | O'Herron |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0106402 A1 | 5/2006 | McLucas |
| 2006/0149137 A1 | 7/2006 | Pingleton et al. |
| 2006/0149306 A1 | 7/2006 | Hart et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 * | 11/2006 | Hess et al. ............ 600/426 |
| 2006/0258899 A1 | 11/2006 | Gill et al. |
| 2006/0264706 A1 | 11/2006 | Piskun |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0185387 A1 | 8/2007 | Albrecht et al. |
| 2007/0203398 A1 | 8/2007 | Bonadio et al. |
| 2007/0255219 A1 | 11/2007 | Vaugh et al. |
| 2007/0299387 A1 | 12/2007 | Williams et al. |
| 2008/0027476 A1 | 1/2008 | Piskun |
| 2008/0097162 A1 | 4/2008 | Bonadio et al. |
| 2008/0097163 A1 | 4/2008 | Butler et al. |
| 2008/0255519 A1 * | 10/2008 | Piskun et al. ............ 604/174 |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0149714 A1 | 6/2009 | Bonadio |
| 2009/0187079 A1 * | 7/2009 | Albrecht et al. ............ 600/206 |
| 2009/0292176 A1 | 11/2009 | Bonadio et al. |
| 2009/0326330 A1 | 12/2009 | Bonadio et al. |
| 2010/0057121 A1 | 3/2010 | Piskun et al. |
| 2010/0063362 A1 | 3/2010 | Bonadio et al. |
| 2010/0063364 A1 | 3/2010 | Bonadio et al. |
| 2010/0081880 A1 * | 4/2010 | Widenhouse et al. ........ 600/201 |
| 2010/0081881 A1 * | 4/2010 | Murray et al. ............ 600/203 |
| 2010/0113886 A1 * | 5/2010 | Piskun et al. ............ 600/231 |
| 2010/0204548 A1 | 8/2010 | Bonadio et al. |

(56) References Cited

U.S. PATENT DOCUMENTS

| | | | |
|---|---|---|---|
| 2010/0217087 A1 | 8/2010 | Bonadio et al. | |
| 2010/0274091 A1* | 10/2010 | Rothstein et al. | 600/201 |
| 2010/0274093 A1* | 10/2010 | Shelton, IV | 600/206 |
| 2010/0280326 A1 | 11/2010 | Hess et al. | |
| 2011/0270195 A1* | 11/2011 | Piskun | 604/165.01 |
| 2012/0022333 A1* | 1/2012 | Main et al. | 600/201 |
| 2013/0245373 A1* | 9/2013 | Okoniewski | 600/109 |

FOREIGN PATENT DOCUMENTS

| | | |
|---|---|---|
| DE | 296 00 939 | 6/1998 |
| EP | 0113520 | 7/1984 |
| EP | 0142262 | 5/1985 |
| EP | 0537768 | 4/1993 |
| EP | 0950376 | 10/1999 |
| EP | 1118657 | 7/2001 |
| EP | 1312318 | 5/2003 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 11-290327 | 10/1999 |
| JP | 2001-61850 | 3/2001 |
| JP | 2002-28163 | 1/2002 |
| JP | 2004-509659 | 4/2004 |
| JP | 2004-195037 | 7/2004 |
| RU | SU 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/91652 | 12/2001 |
| WO | WO 01/91653 | 12/2001 |
| WO | WO 02/17800 A2 | 3/2002 |
| WO | WO 02/34108 A2 | 5/2002 |
| WO | WO 03/026512 A1 | 4/2003 |
| WO | WO 03/034908 A3 | 5/2003 |
| WO | WO 03/061480 A1 | 7/2003 |
| WO | WO 03/103548 A1 | 12/2003 |
| WO | WO 2004/026153 A1 | 4/2004 |
| WO | WO 2004/030547 A1 | 4/2004 |
| WO | WO 2005/009257 A2 | 2/2005 |
| WO | WO 2005/034766 A2 | 4/2005 |
| WO | WO 2005/089661 | 9/2005 |
| WO | WO 2006/040748 A1 | 4/2006 |
| WO | WO 2006/059318 | 8/2006 |
| WO | WO 2008/121294 A1 | 10/2008 |
| WO | WO 2009/035663 A2 | 3/2009 |
| WO | WO 2014/144233 A1 | 9/2014 |

OTHER PUBLICATIONS

International Search Report dated Dec. 3, 2010 from International Application No. PCT/IE2010/000055 (5 pages).

* cited by examiner

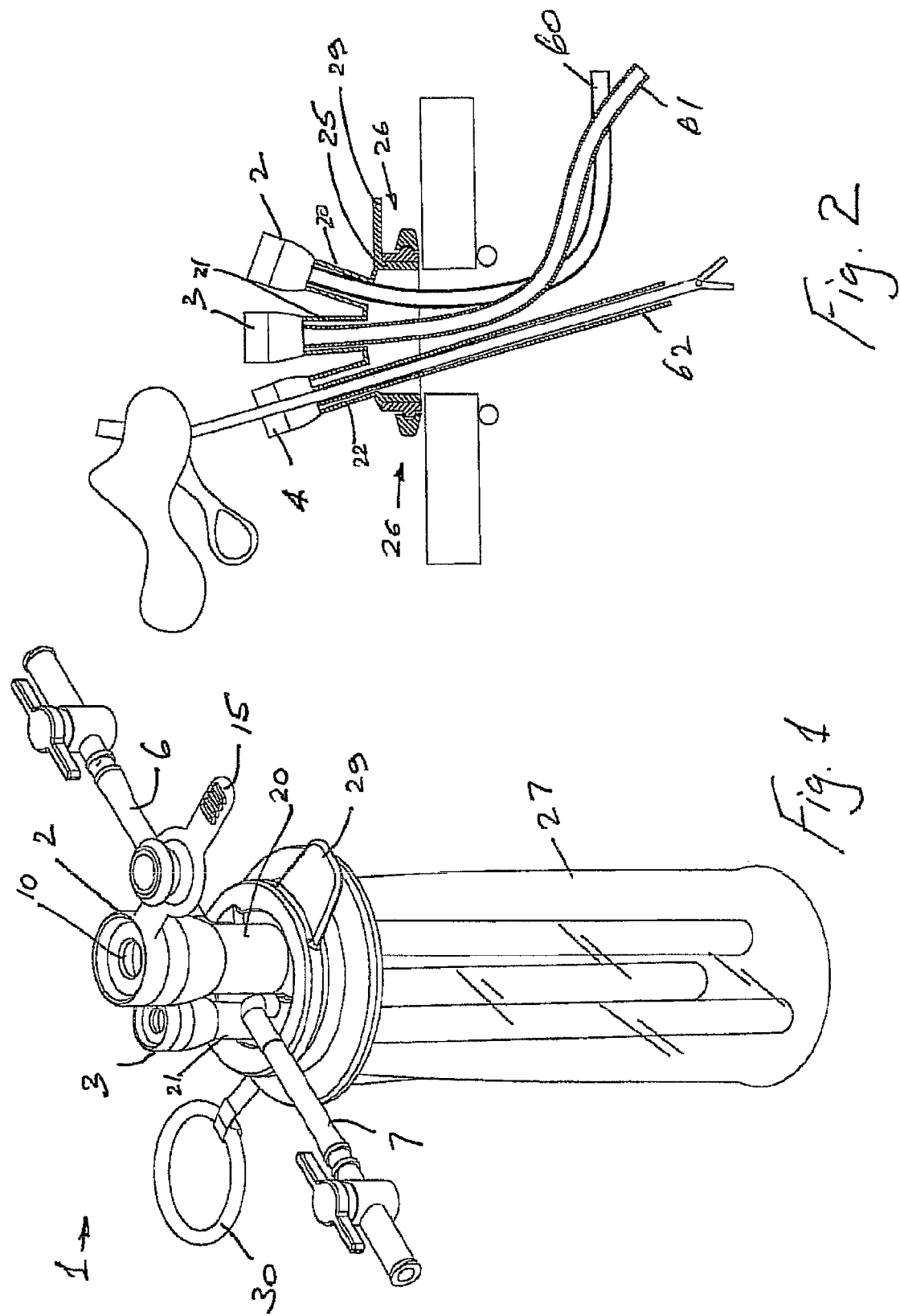

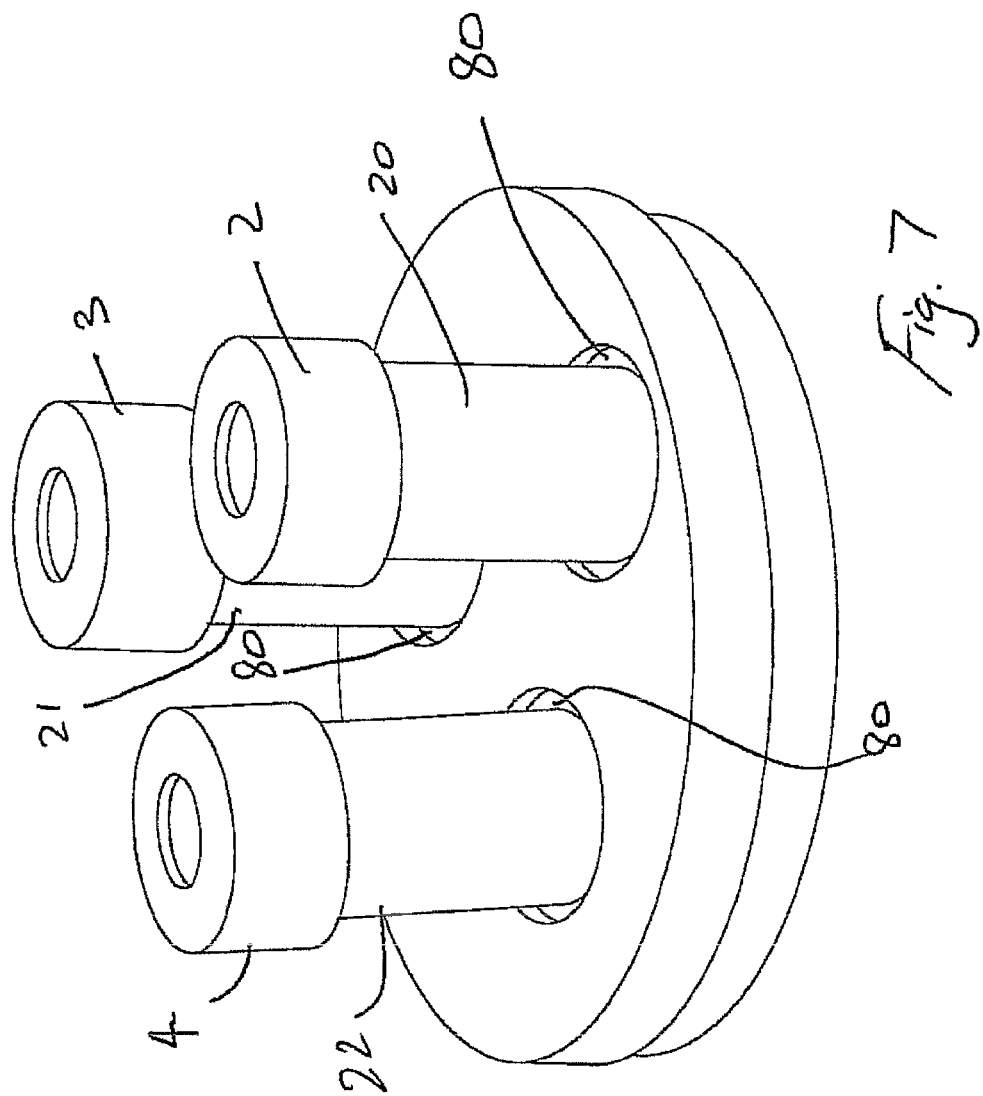

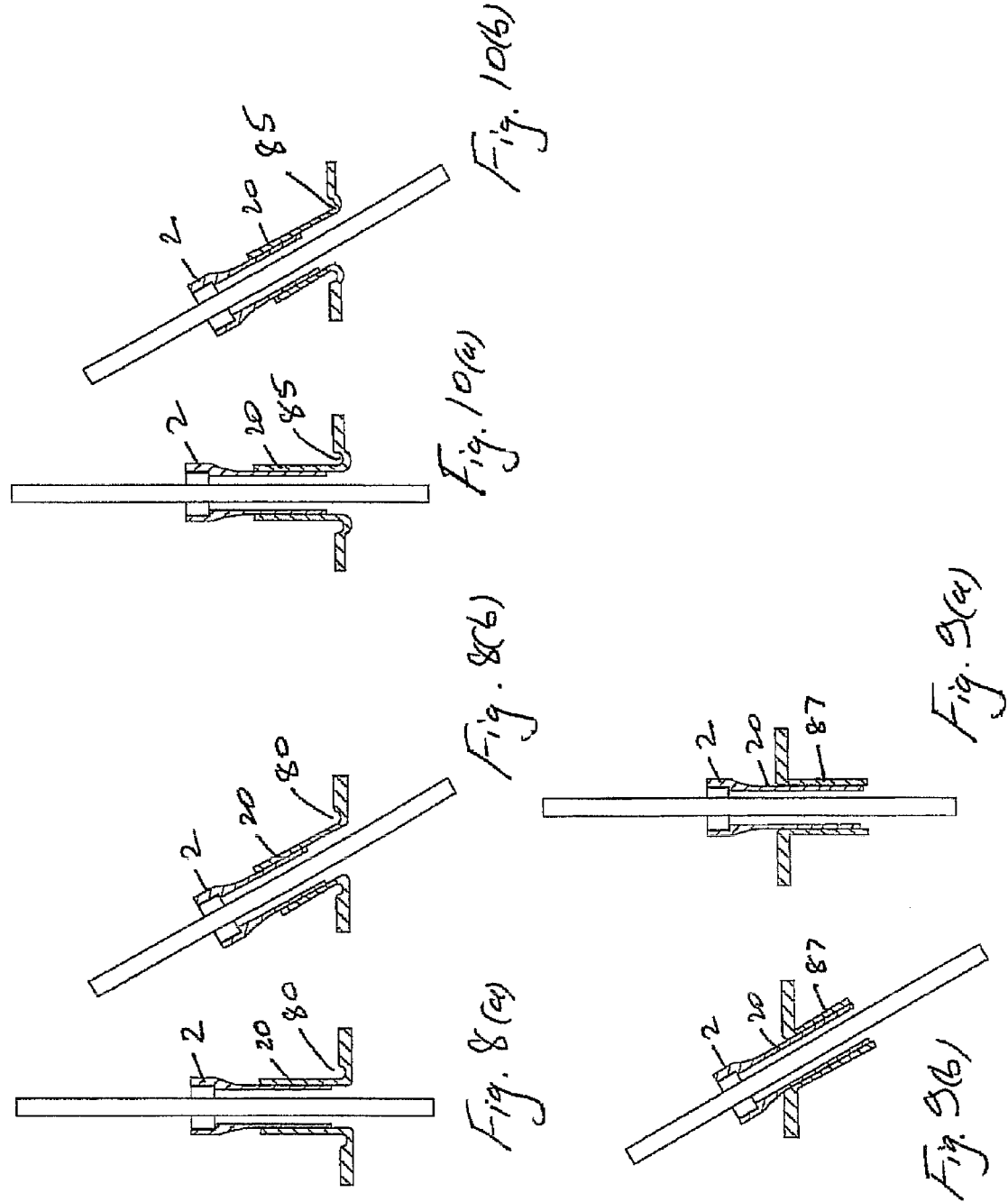

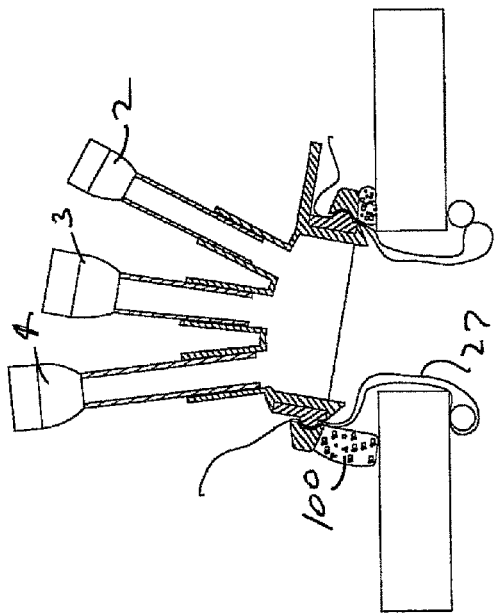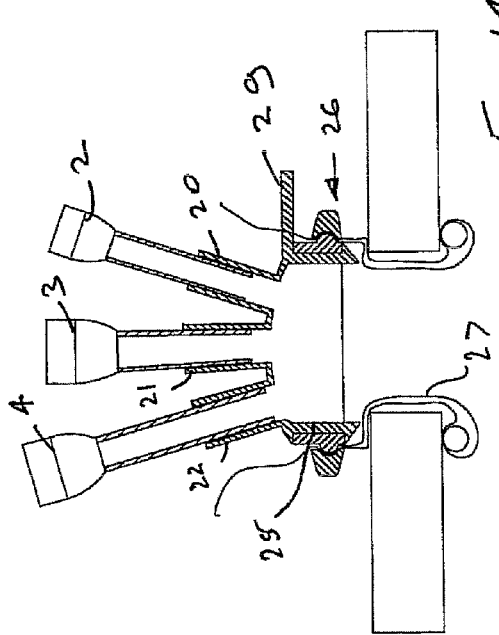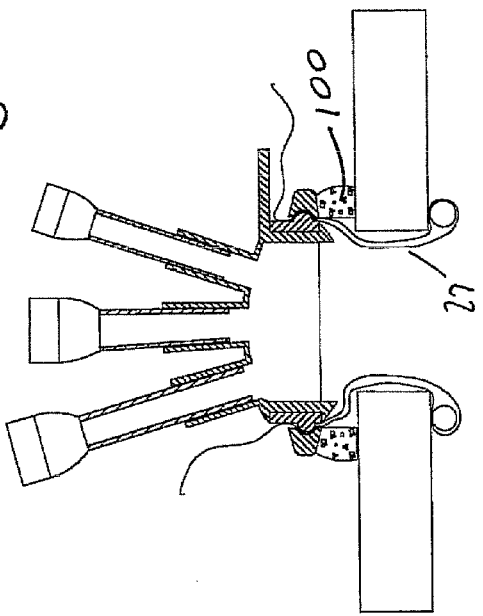

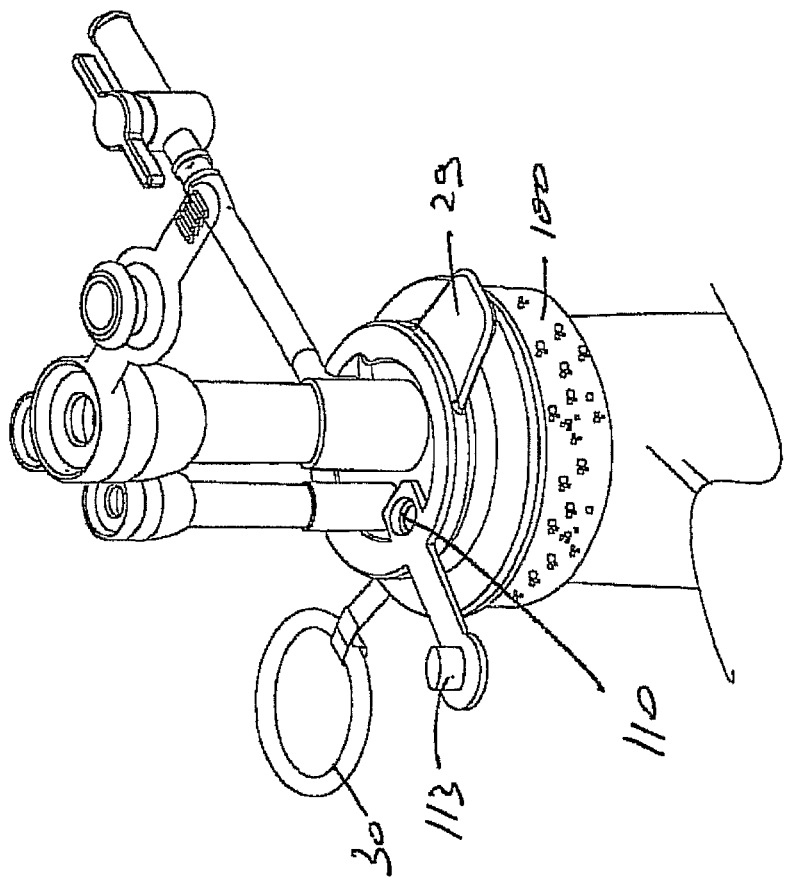
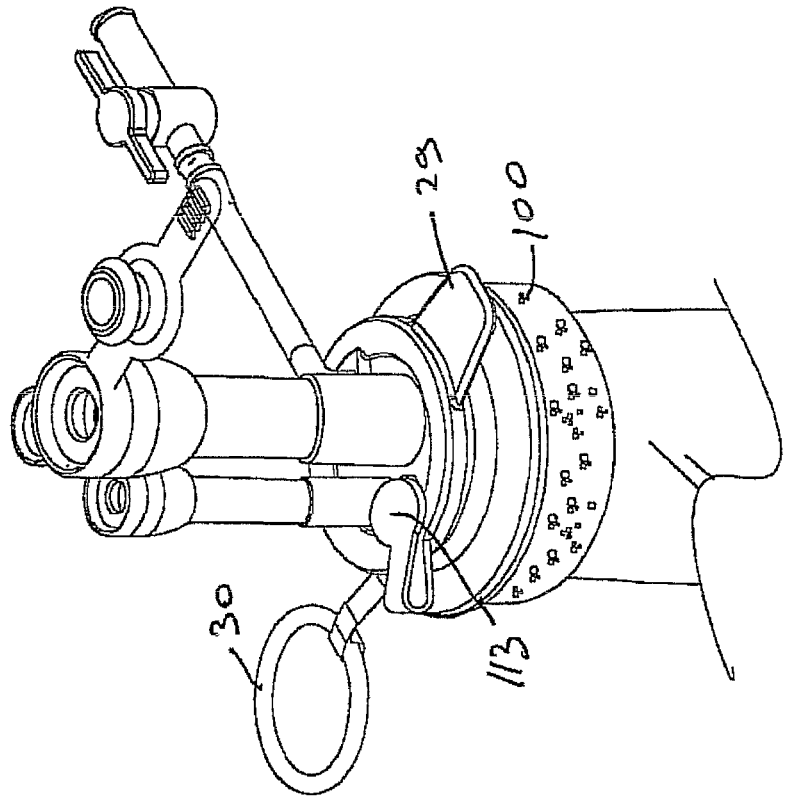

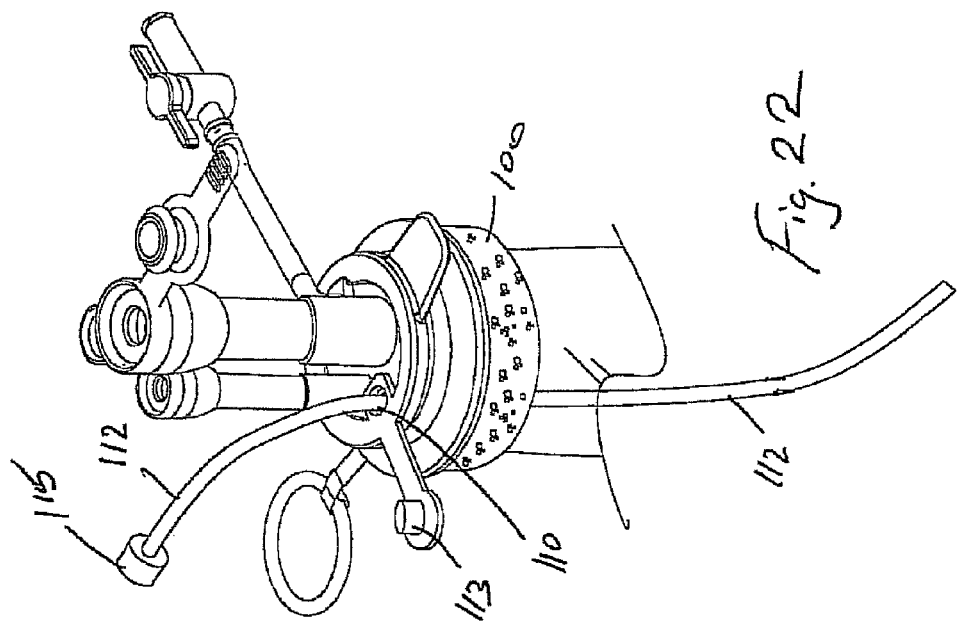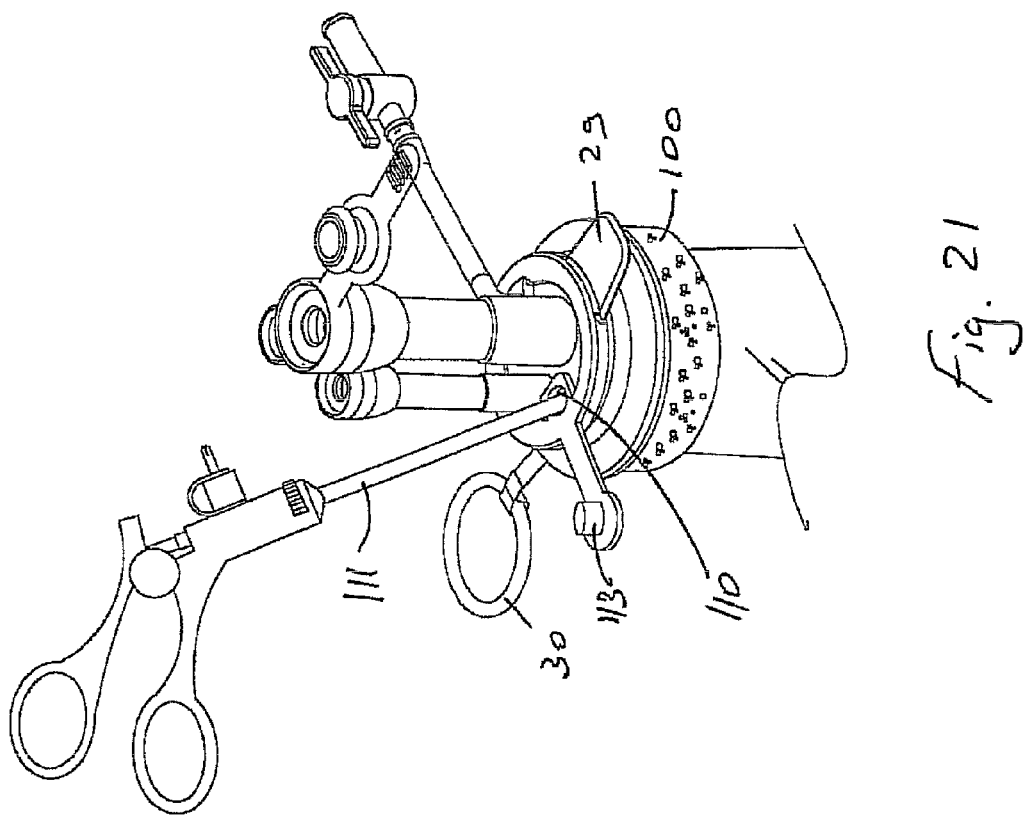

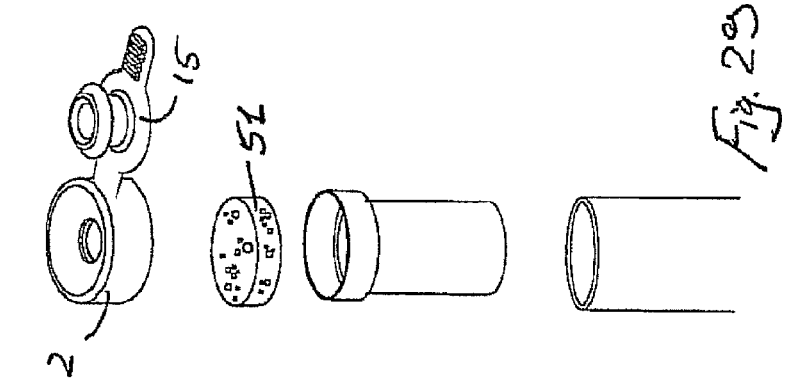
Fig. 28
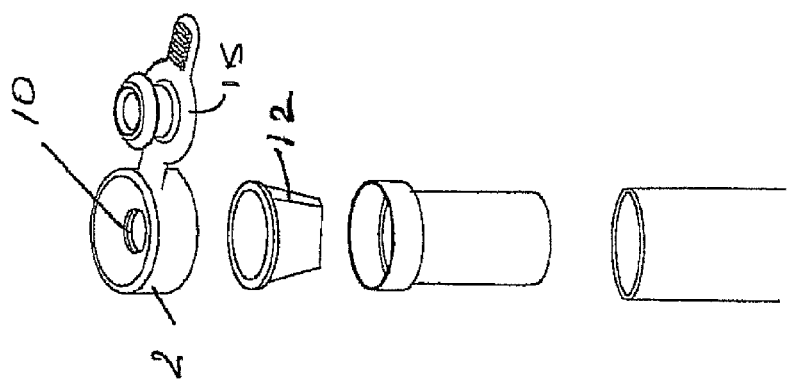
Fig. 27
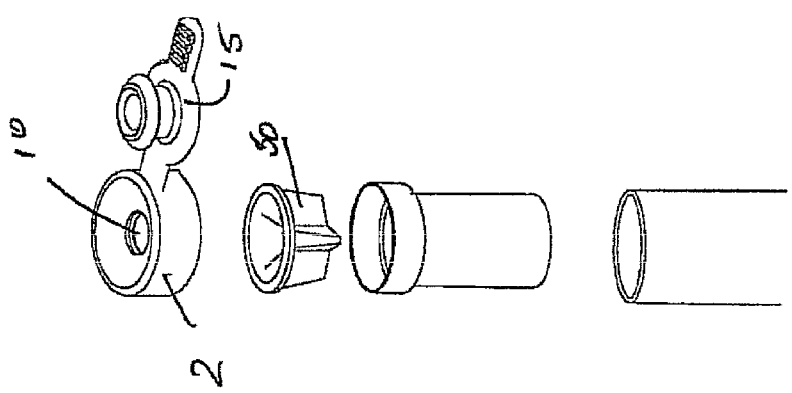
Fig. 25
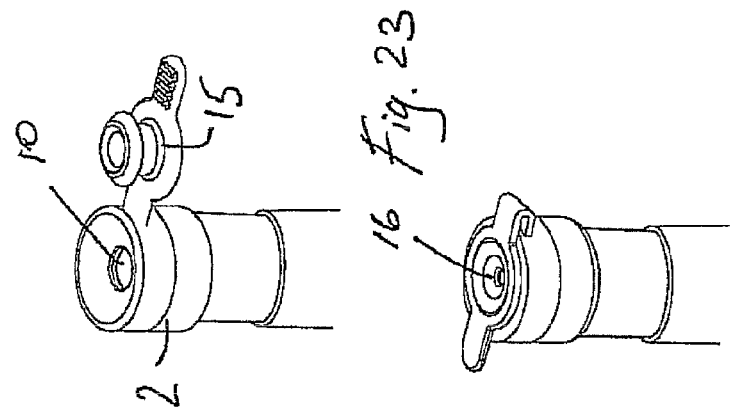
Fig. 23
Fig. 24

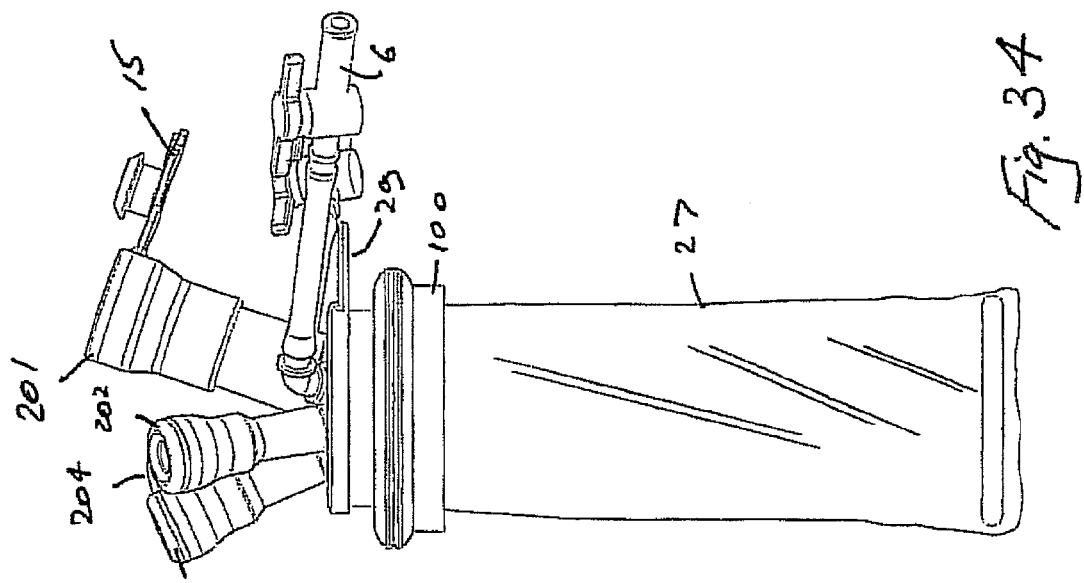
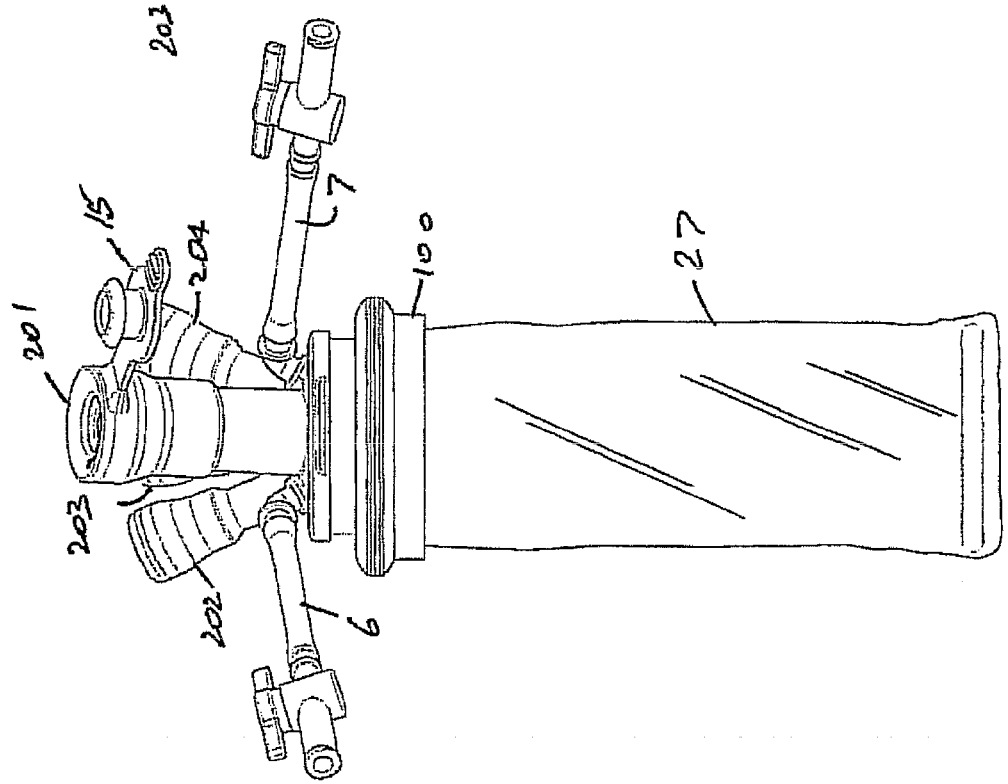

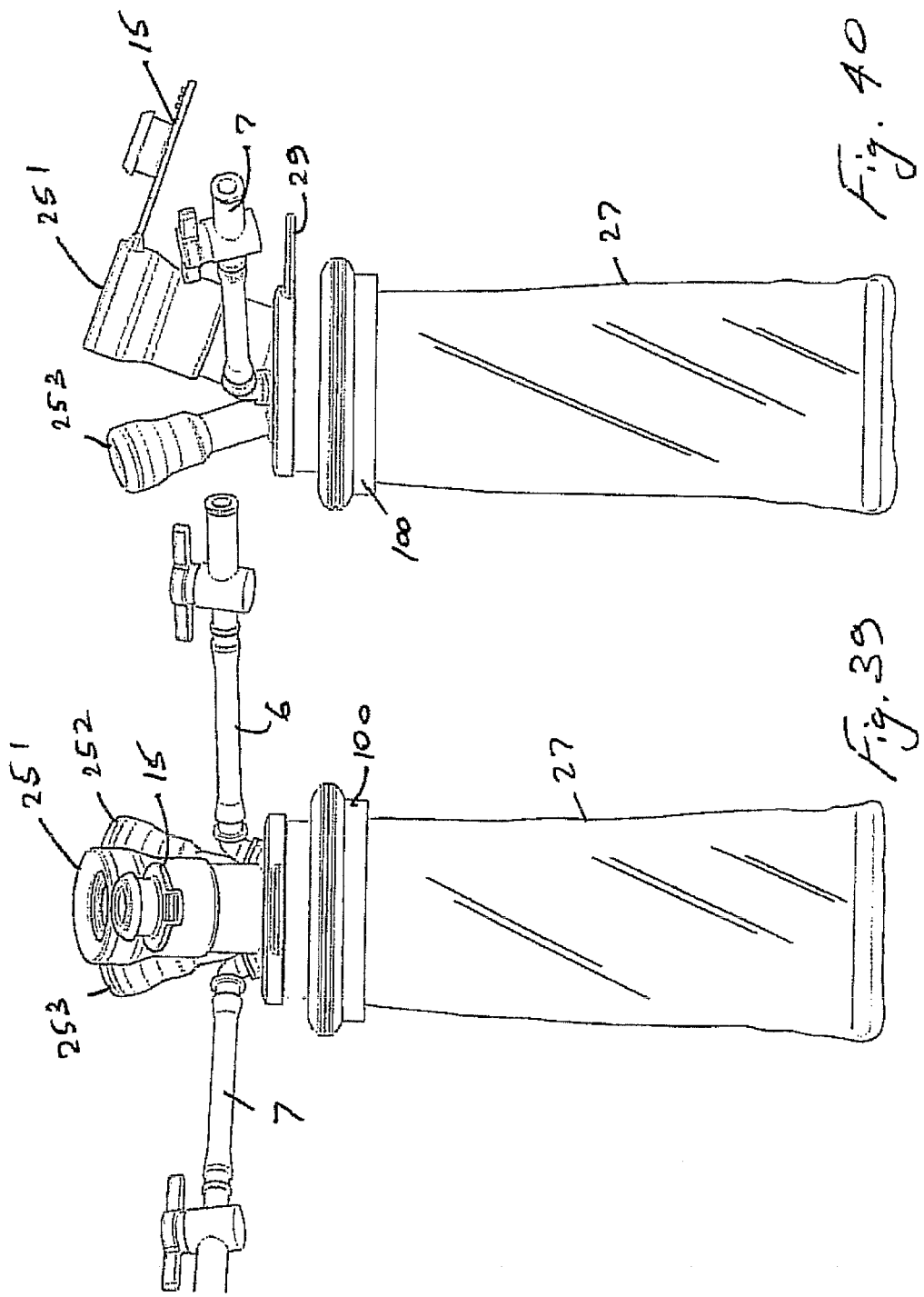

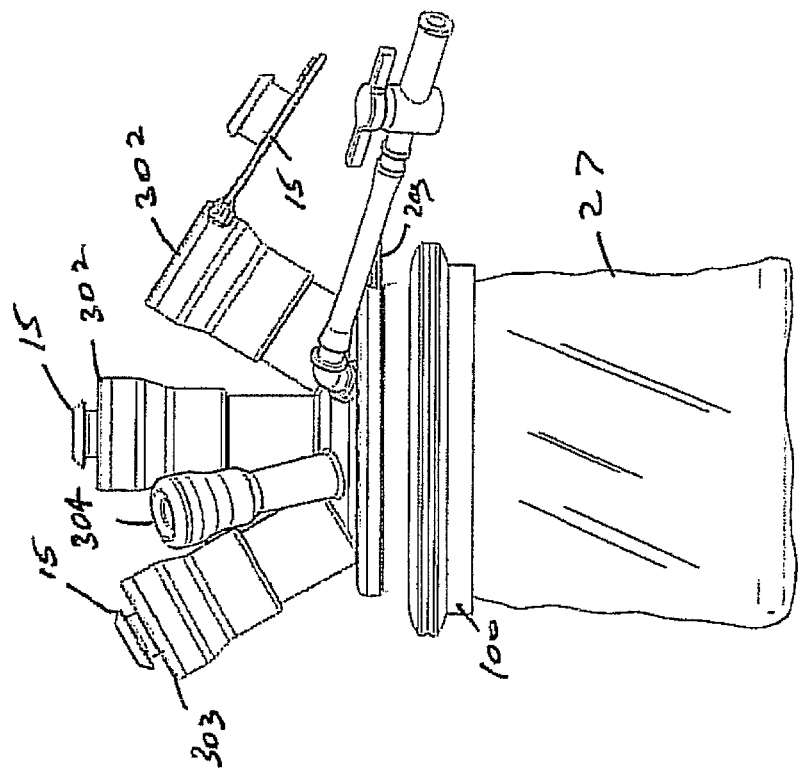
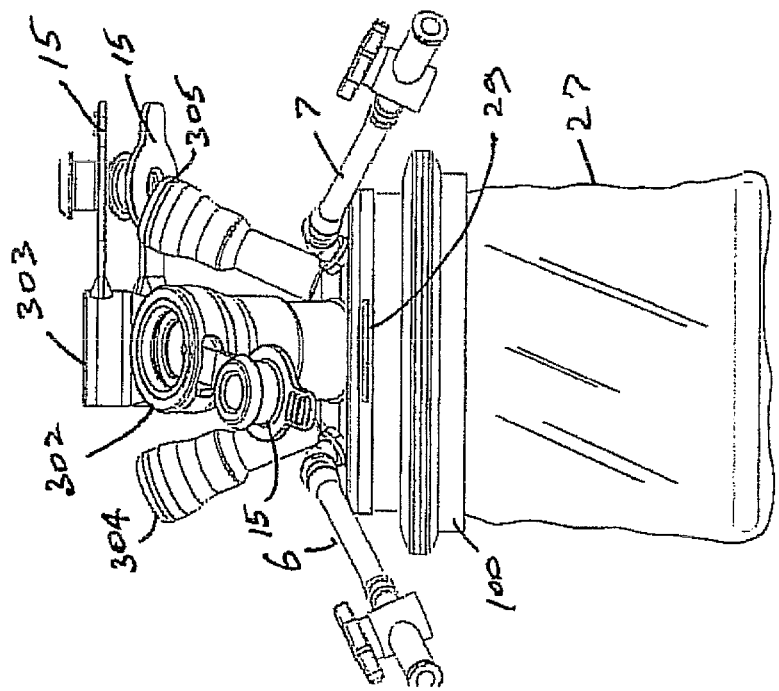

INSTRUMENT ACCESS DEVICE

This application is a Continuation of U.S. patent application Ser. No. 12/885,011, filed Sep. 17, 2010 now abandoned, which is a Continuation-In-Part of U.S. patent application Ser. No. 12/694,888, filed Jan. 27, 2010 now U.S. Pat. No. 8,657,740, which claims the benefit of Provisional Application No. 61/147,625, filed Jan. 27, 2009, and Provisional Application No. 61/147,613 filed Jan. 27, 2009.

U.S. patent application Ser. No. 12/694,888 is also a Continuation-In-Part of U.S. patent application Ser. No. 12/133,827, filed Jun. 5, 2008 now U.S. Pat. No. 8,187,178, which claims the benefit of Provisional Application Nos. 60/924,918, filed Jun. 5, 2007; 60/935,625 filed Aug. 22, 2007; and 60/996,760 filed Dec. 4, 2007.

U.S. patent application Ser. No. 12/885,011 also claims the benefit of U.S. Provisional Application No. 61/243,295 filed on Sep. 17, 2009. The content of all of the above applications is incorporated herein by reference.

INTRODUCTION

The invention relates to an instrument insertion device and an instrument access system incorporating the instrument insertion device.

STATEMENTS OF INVENTION

According to the invention there is provided an instrument access device comprising: —
 a proximal member for location externally of an opening into a body cavity;
 a first instrument receiver for receiving an instrument; and
 a second instrument receiver for receiving an instrument.

In one embodiment the device comprises a first connector extending between the proximal member and the first instrument receiver. There may be a second connector extending between the proximal member and the first instrument receiver.

In one embodiment at least one of the connectors is substantially rigid.

In one case a joint between at least one of the connectors and the proximal member which facilitates movement of the connector relative to the proximal member.

The joint may facilitate pivotal or swivelling movement of the connector.

In one case the joint is substantially a universal joint.

In one embodiment the device comprises a formation between the connector and the proximal member to facilitate relative movement between the connector and the proximal member. The formation may comprise a groove.

In another embodiment the device comprises a spacer for location between the proximal member and the outside of a wound opening. The spacer may be flexible. The spacer may be of flexible material. The spacer may comprise a pad which may comprise foam, rubber, or the like.

In one aspect of the invention there is provided an instrument access device comprising a proximal member for location externally of an opening into a body cavity, a first instrument receiver for receiving an instrument, a second instrument receiver for receiving an instrument, a proximal mounting for location outside of a wound opening, the proximal member being releasably mounted to the proximal mounting and a flexible spacer for location between the proximal mounting and the outside of a wound opening.

In one embodiment at least one of the connectors comprises an instrument seal.

In another embodiment the device comprises a flexible cannula extending from at least one of the connectors. The flexible cannula may be attached to the connector.

The cannula may be movable relative to the connector. For example, the cannula may be slidable relative to the connector.

In another embodiment the device comprises a third instrument receiver for receiving an instrument and a third connector extending between the proximal member and the first instrument receiver.

In a further embodiment the device comprises a port such as an opening in the proximal member which is sized to receive a small instrument or a tube. The opening may be a diameter of from 1 to 5 mm, typically from 2 to 4 mm.

In one case the opening has a valve means. There may be a cap for the opening.

In another embodiment at least one of the connectors has an associated seal or valve. The seal may comprise a first valve and a second valve distal of the first valve.

In one case the first valve comprises a lip-seal valve.

The second valve may comprise at least two cusps such as a duckbill valve.

In one case the lipseal is provided in a lipseal housing and the second valve is provided in a second seal housing. The lipseal housing may be movable relative to the second seal housing. The lip seal housing may comprise a cap for the second seal housing. In one case the lipseal housing is removable from the second seal housing. The lipseal housing may be releasably connected to the second seal housing. The lipseal housing may be connected to the second seal housing by a hinge connection such as a strap. The lipseal housing may comprise a reducer cap.

In one embodiment the device comprises a distal anchoring member for location within a wound interior; and a retractor member extending proximally from the distal anchoring member to retract laterally the sides of a wound opening.

The retractor member may extend at least between the distal anchoring member and the proximal member. The retractor member may extend in two layers between the distal anchoring member and the proximal member.

In one case a first end portion of the retractor member is fixed to the proximal member.

The retractor member may be movable relative to the distal anchoring member. A second end portion of the retractor member may be movable relative to the proximal member.

In one embodiment the retractor member extends distally from the proximal member to the distal anchoring member, is looped around the distal anchoring member, and extends proximally from the distal anchoring member to the proximal member.

The proximal member may comprise an inner part and an outer part. The retractor member may extend between the inner part and the outer part.

In one embodiment the device comprises a mounting member for mounting to the proximal member. The mounting member may be releasably mounted to the proximal member. The mounting member may be mounted to the proximal member in an interference fit arrangement. The mounting member may be mounted to the proximal member in a snap-fit arrangement.

In one case the device comprises a clamp to clamp the mounting member to the proximal member.

It will be appreciated that features described with reference to one embodiment of the invention may be utilised with any of the other embodiments.

BRIEF DESCRIPTION OF THE DRAWINGS

The invention will be more clearly understood from the following description of some embodiments thereof, given by way of example only, with reference to the accompanying drawings, in which:—

FIG. 1 is an isometric view of an instrument access device according to one embodiment of the invention;

FIG. 2 is a cross sectional view of the device of FIG. 1, in use;

FIG. 7 is an isometric view of part of an instrument access device of the invention;

FIGS. 8a and 8b are cross sectional views of part of the device according to one embodiment in different configurations of use;

FIGS. 9a and 9b are cross sectional views of part of the device according to another embodiment in different configurations of use;

FIGS. 10a and 10b are cross sectional views of part of the device according to a further embodiment in different configuration of use;

FIGS. 14 to 18 are cross sectional views illustrating some of the devices of the invention, in use;

FIGS. 19 and 20 are isometric views of another instrument access device of the invention;

FIGS. 21 and 22 are views of the device of FIGS. 19 and 20 in different uses;

FIGS. 23 and 24 are isometric views of a valve assembly of an instrument access device;

FIG. 25 is an exploded isometric view of one valve assembly;

FIG. 27 is an exploded isometric view of another valve assembly;

FIG. 29 is an exploded isometric view of a further valve assembly;

FIG. 34 is an elevational view from one side of the device of FIG. 32;

FIG. 35 is an elevational view from another side of the device of FIG. 32;

FIGS. 39 and 40 are elevational views from opposite sides of the assembled device of FIGS. 36 to 38;

FIGS. 44 and 45 are elevational views from opposite sides of the device of FIG. 42;

DETAILED DESCRIPTION

Figure 4:
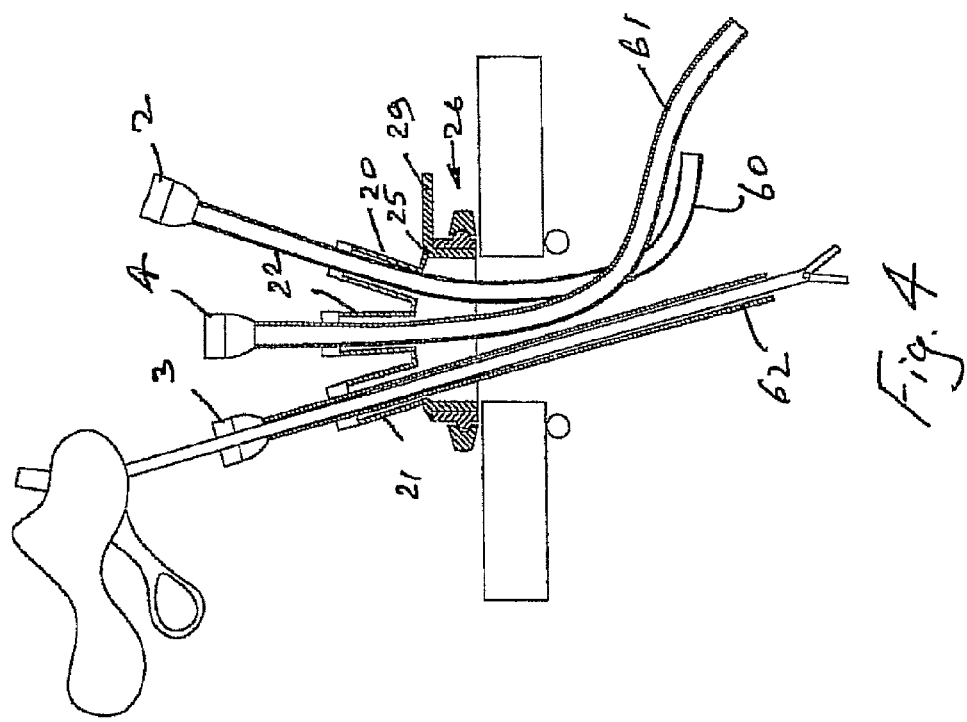
FIG. 4 is a cross sectional view of the device of FIG. 3, in use.

Referring to the drawings and initially to FIGS. 1 and 2 there is illustrated an instrument access device 1 according to the invention which in this case comprises three instrument insertion sealing devices according to the invention. The access device 1 comprises a first instrument insertion device 2, a second instrument insertion device 3, and a third instrument insertion device 4. The access device in this case also has two insufflation/desufflation ports 6, 7.

The insertion device 2 comprises a lipseal 10 through which an instrument 11 is insertable and a second seal member 12 having a passageway extending therethrough, through which the instrument 11 is insertable. The first insertion device 2 also has a reducer cap 15 which has a further lipseal 16 which is smaller than the lipseal 10. To insert large diameter instruments, the cap 15 is removed. To insert smaller diameter instruments the cap 15 is in place.

Figure 28:
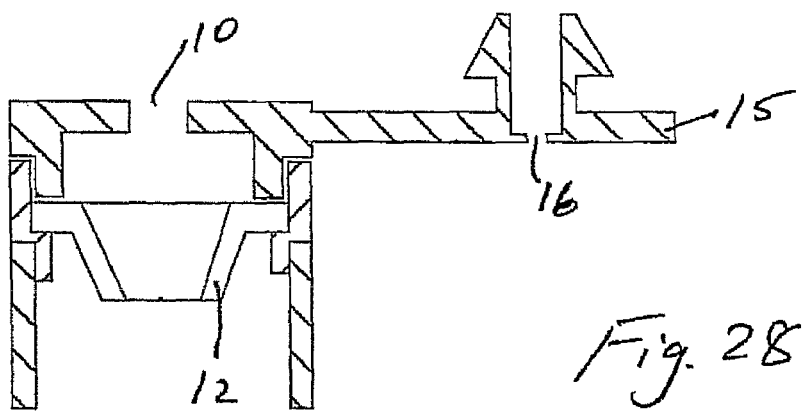
FIG. 28 is a cross sectional view of part of the valve assembly of FIG. 27.

Referring to FIGS. 27 and 28 the second seal member 12 may comprise a duckbill valve through which the instrument 11 passes. The duckbill valve 12 provides sealing engagement with the instrument shaft whilst accommodating lateral movement of the instrument as illustrated.

Figure 26:
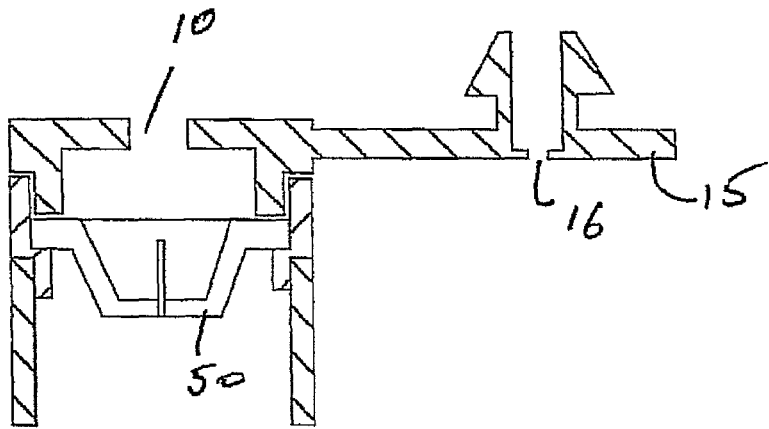
FIG. 26 is a cross sectional view of part of the valve assembly of FIG. 25.
Figure 30:
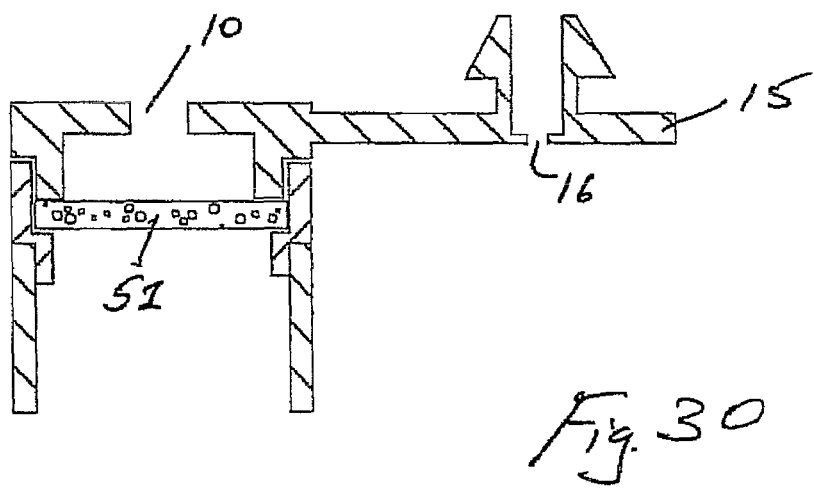
FIG. 30 is a cross sectional view of part of the valve assembly of FIG. 29.
Figure 31:
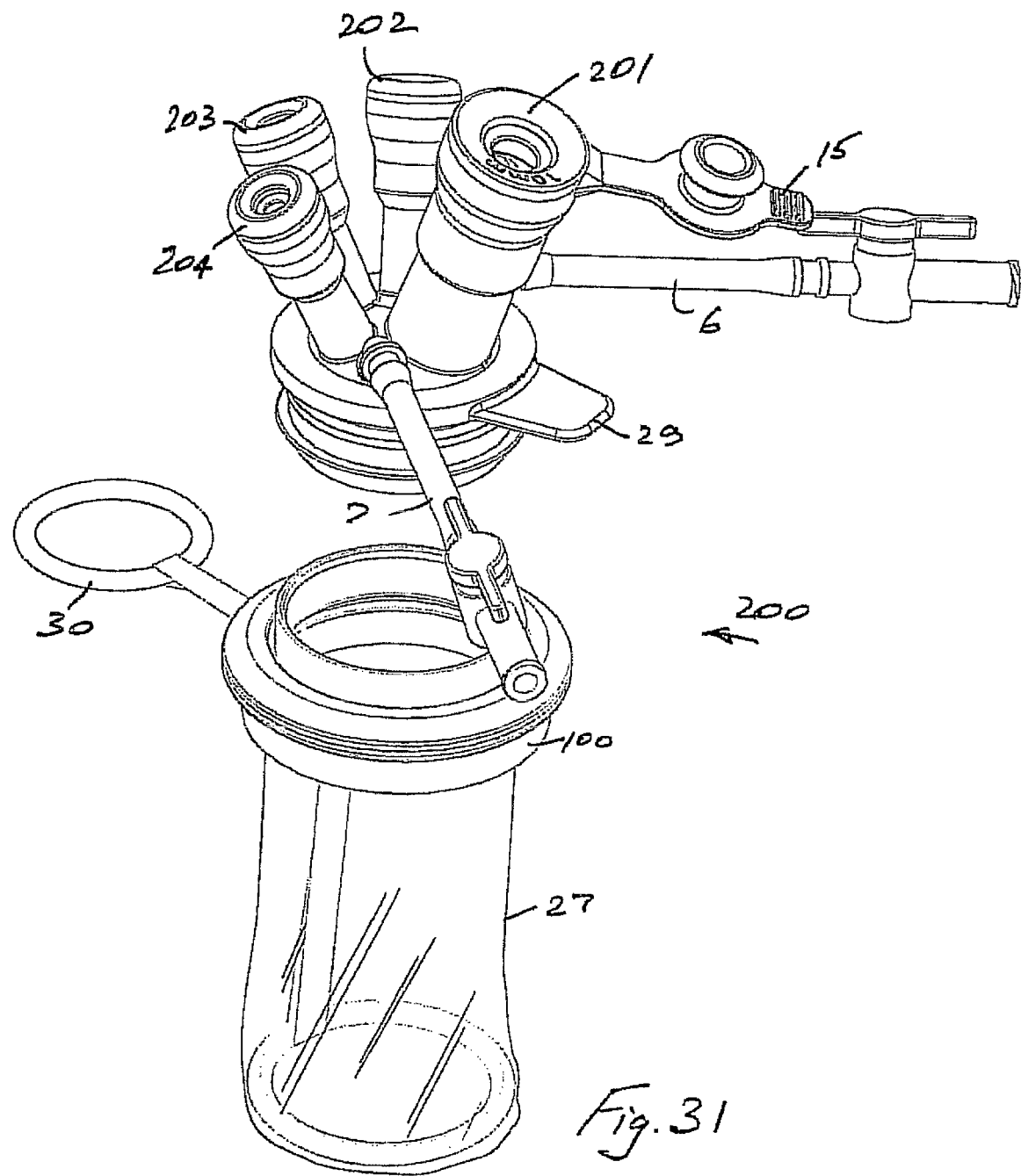
FIG. 31 is an exploded perspective view of another instrument access device according to the invention.
Figure 32:
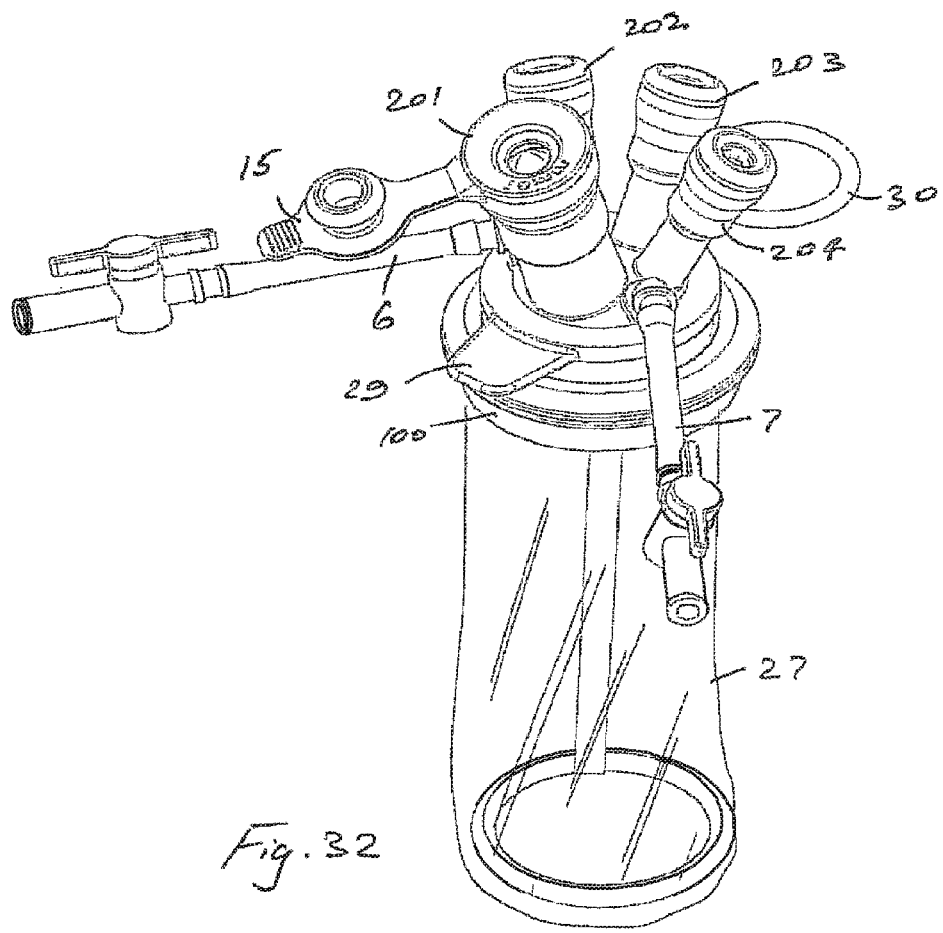
FIG. 32 is a perspective view of the device of FIG. 31 assembled.
Figure 33:
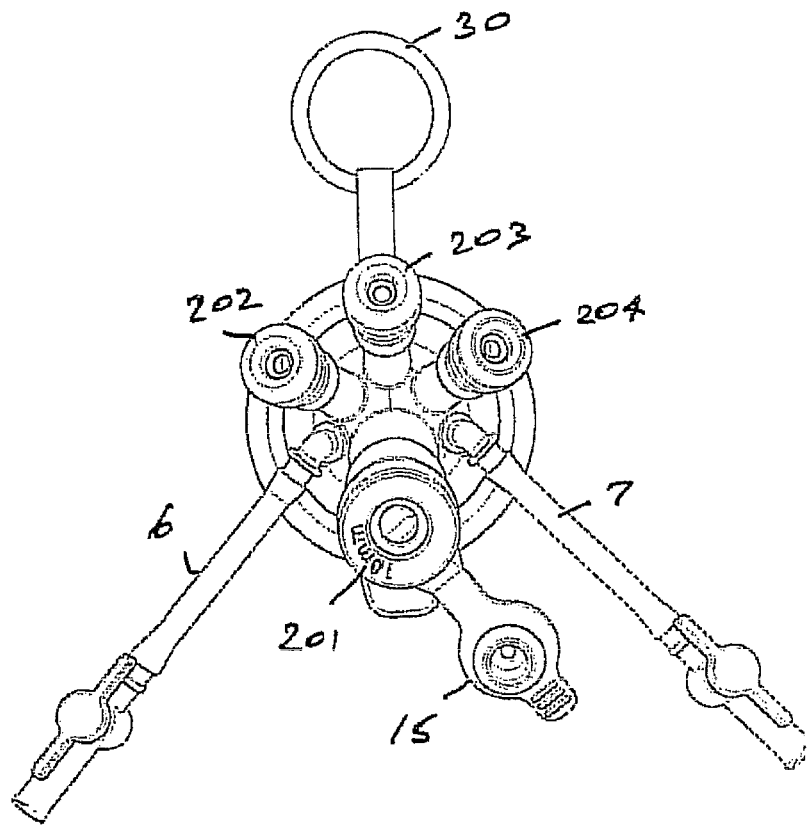
FIG. 33 is a top plan view of the device of FIG. 32.
Figure 36:
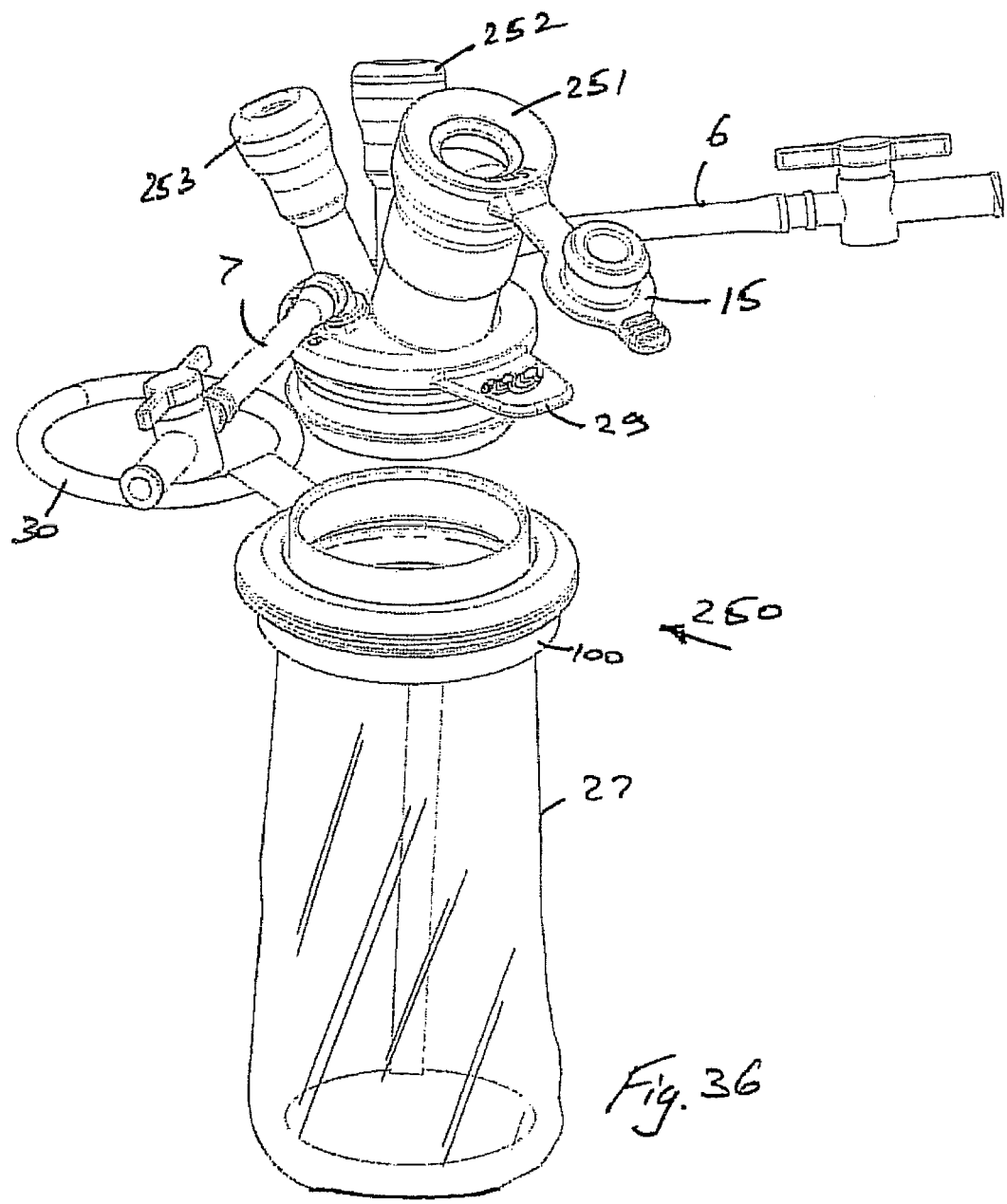
FIGS. 36 and 37 are exploded perspective views of a further instrument access device according to the invention.
Figure 37:
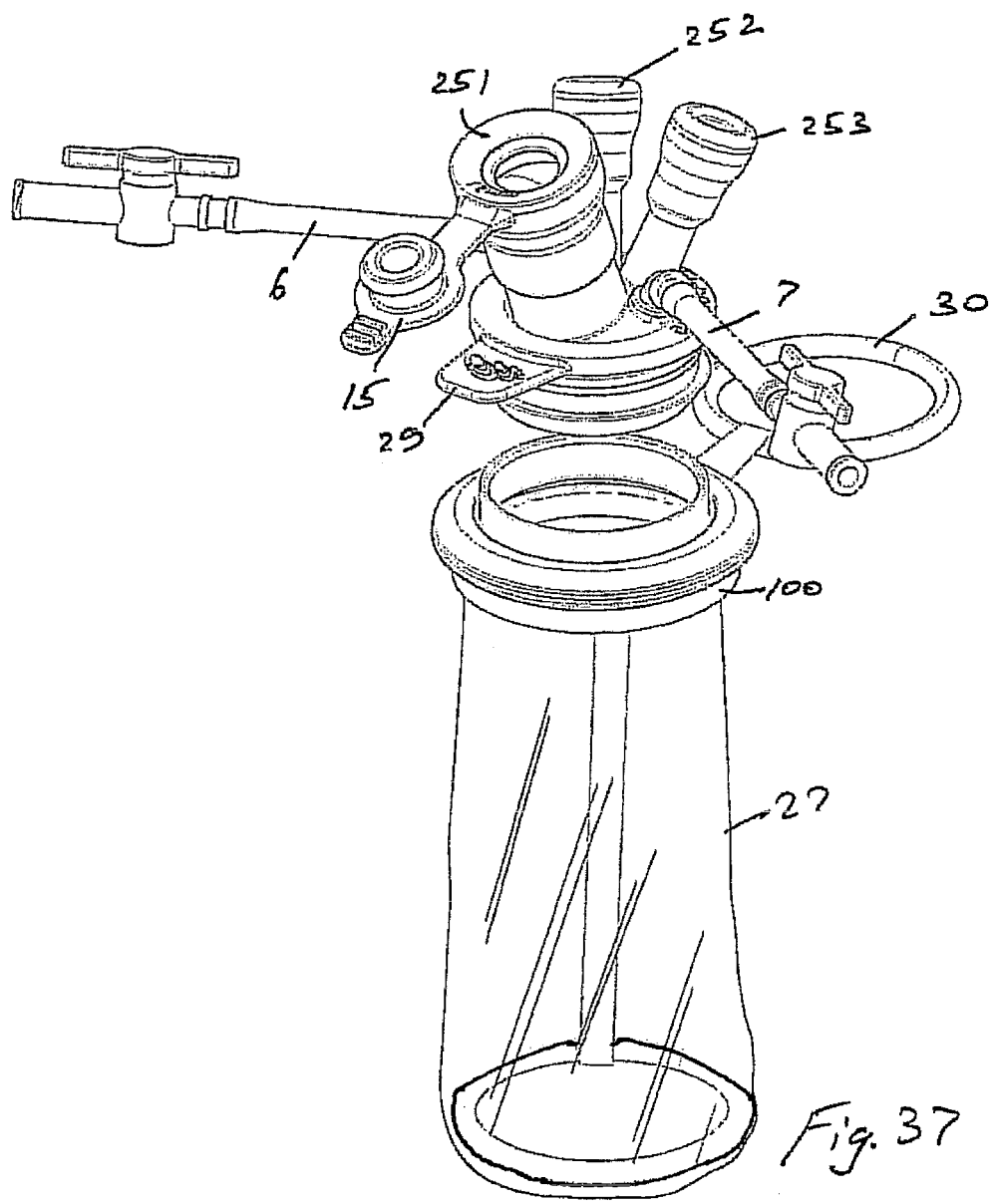
Figure 38:
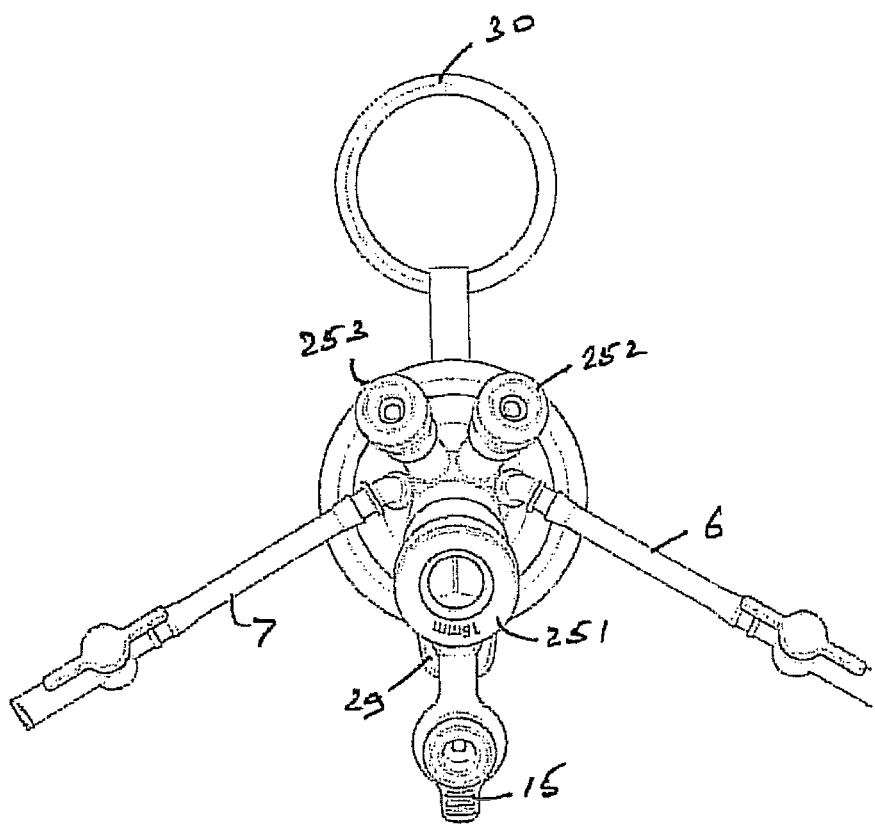
FIG. 38 is a top plan view of the device of FIGS. 36 and 37.
Figure 41:
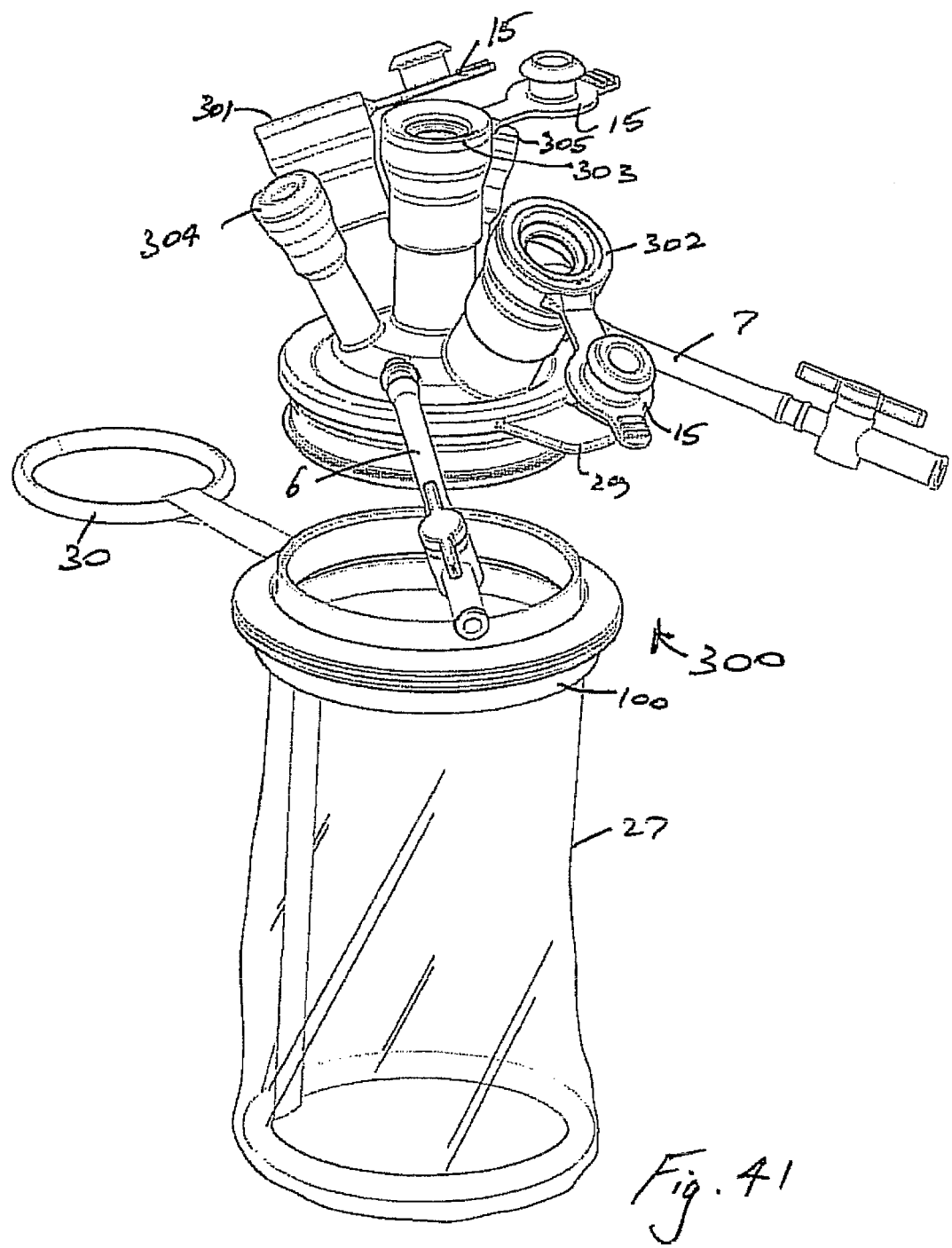
FIG. 41 is an exploded perspective view of another instrument access device according to the invention.
Figure 42:
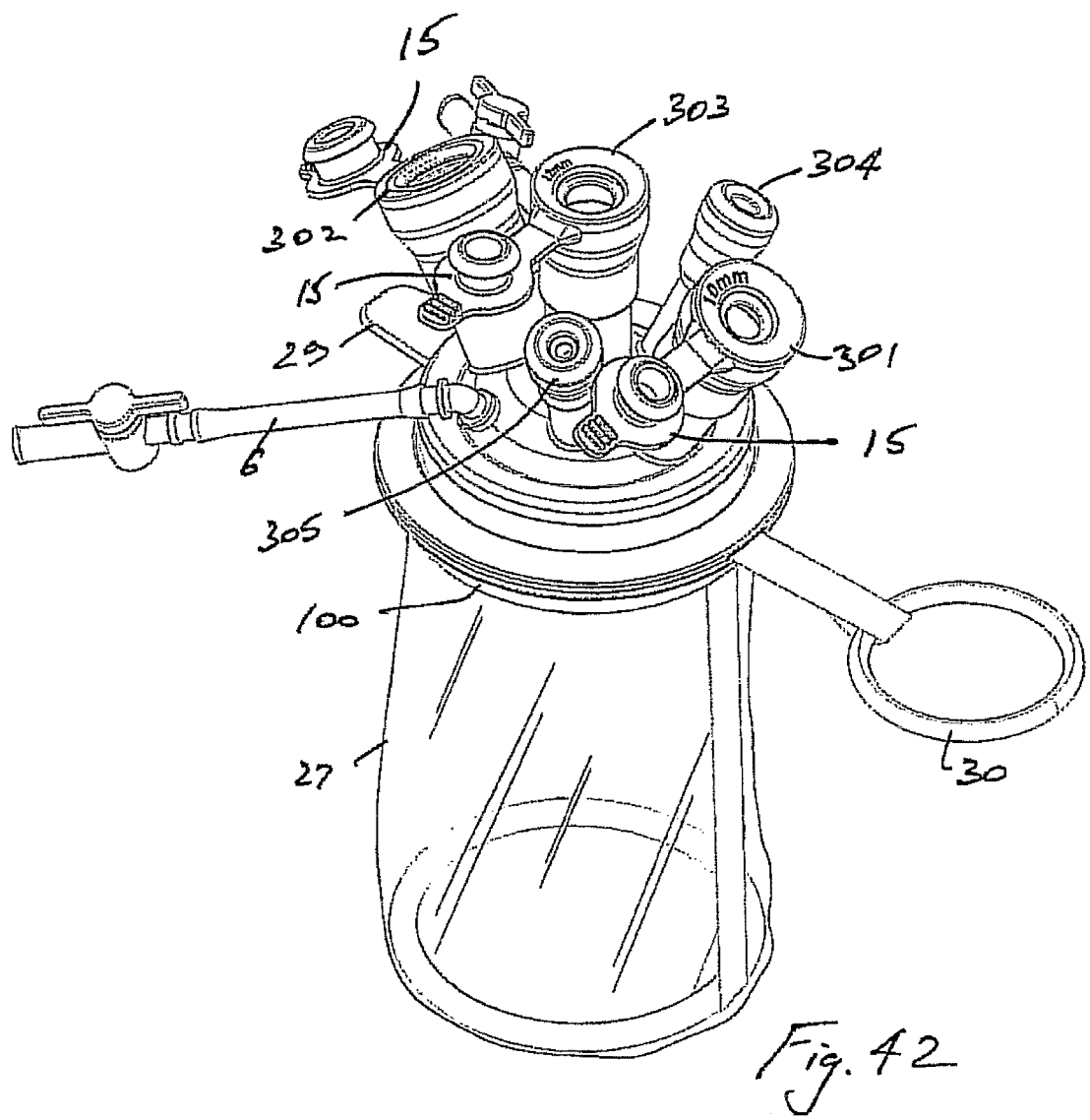
FIG. 42 is a perspective view of the device of FIG. 41 assembled.
Figure 43:
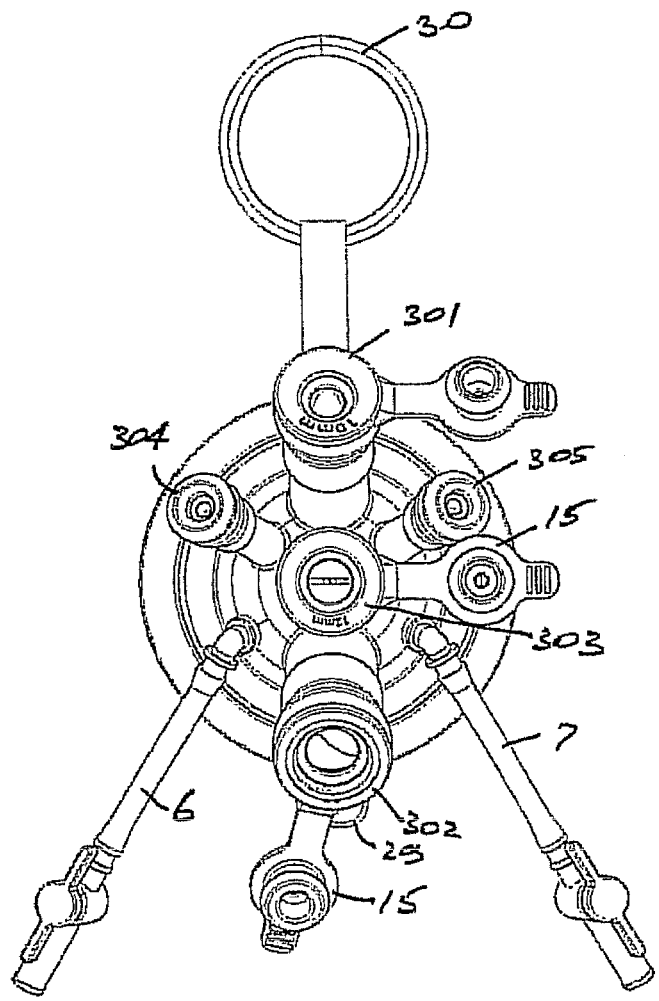
FIG. 43 is a top plan view of the device of FIG. 42.

Alternatively, as illustrated in FIGS. 25 and 26 the second valve may comprise a multicusp valve such as a tricuspid valve 50. In another case as illustrated in FIGS. 29 and 30 the second valve may comprise a foam or gel.

The lipseal valve 10 is located proximally of the duckbill valve 12 so that a double seal is provided to substantially prevent leakage of insufflation gas.

The lipseal 10 may be of any suitable material. For example it may be of an elastomeric material, a foam-type material or a gelatinous material. The duckbill valve 12 may be of any suitable material. For example, it may be of a flexible polymeric material.

The second and third instrument insertion devices 3, 4 may be of the same or different construction as that of the first instrument insertion device 2.

The instrument access device of the invention is suitable for use during laparoscopic surgery to facilitate instrument access to an insufflated abdominal cavity while maintaining pneumoperitoneum.

The instrument access device of the invention comprises a first connector 20 for connecting the first instrument insertion device 2 to a connector base 25, a second connector 21 for connecting the second instrument insertion device 3 to the base 25, and a third connector 22 for connecting the third instrument insertion device 4 to the base 25.

The base 25 is mounted to a proximal ring assembly 26 of a retractor which includes a sleeve 27 which may extend in two layers between a distal anchoring ring (not shown) and the proximal ring assembly 26. One such retractor is described in our US 2005-0090717A, the entire contents of which are incorporated herein by reference. The base 25 has a tab 29 to aid dismounting of the base member 25 from the retractor. A pull ring 30 may be used to aid release of the retractor.

The instrument insertion devices 2, 3, 4 are arranged in sealing relationship to a body of a patient, in use. The instrument seals 2, 3, 4 are spaced proximally of the proximal ring assembly 26.

The connectors 20, 21, 22 connect the proximal ring assembly 26 to the instrument seals 2, 3, 4. The connectors 20, 21, 22 may be integral with the connector base 25 and the seals 2, 3, 4 subsequently attached, for ease of manufacture. In addition, instrument seals 2, 3, 4 can be housed in relatively rigid housings for added strength whilst maintaining connector flexibility.

In use, a wound opening is created in a tissue wall, and the distal anchoring ring is inserted through the wound opening into the wound interior. The proximal ring assembly 26 is located externally of the wound opening, with the retractor member extending proximally from the distal anchoring member through the wound opening. The second end of the retractor member is pulled proximally relative to the proximal ring assembly 26 to retract laterally the sides of the wound opening. Instruments may then be inserted through the instrument seals 2, 3, 4, extended through the connectors 20, 21, 22, and extended through the retracted wound opening and into the wound interior.

Referring especially to FIGS. 1 to 6 in this case the connectors 20, 21, 22 are of a substantially rigid material to aid stability as instruments are inserted and withdrawn.

In the embodiment of FIGS. 1 and 2 the valve assemblies 2, 3, 4 are fixed to their connectors 20, 21, 22 and at least some of the connectors have internal extended flexible cannulae 60, 61 which can be manipulated for ease of positioning of an instrument. One of the connectors may have a more rigid cannula 62 to guide some types of instruments.

Figure 3:
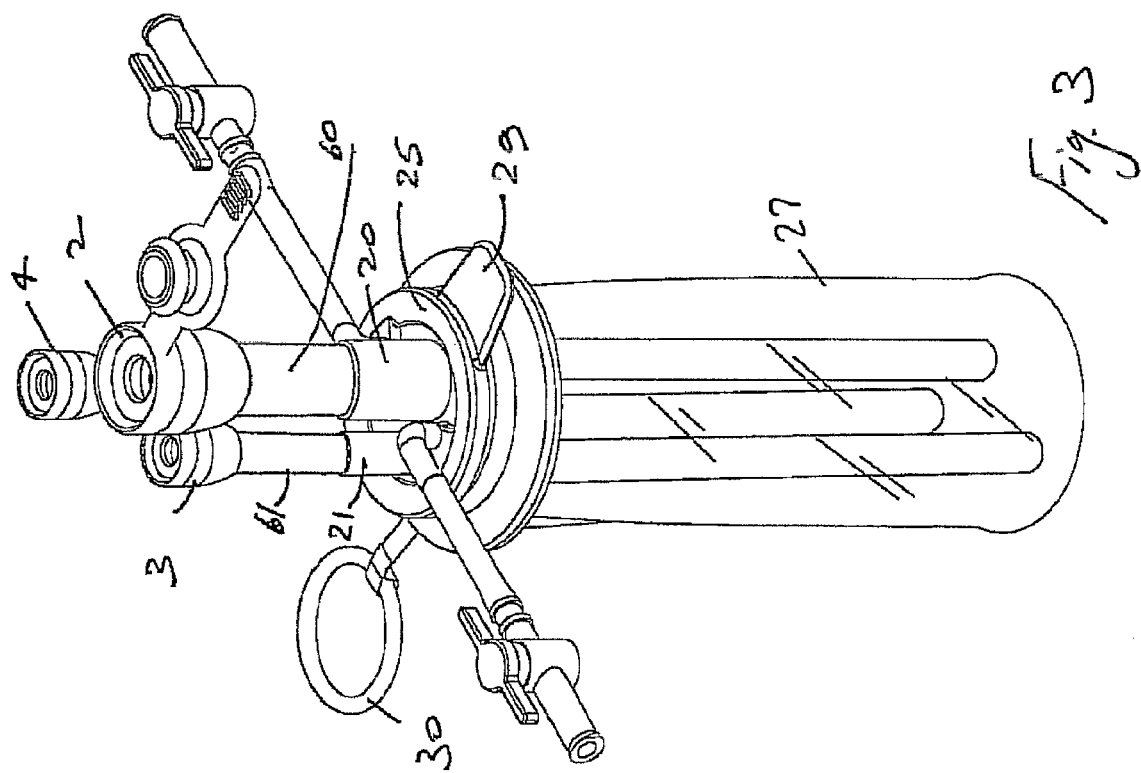
FIG. 3 is an isometric view of an instrument access device according to another embodiment of the invention.

In the case of the devices of FIGS. 1 and 2 one or more of the cannulae 60, 61, 62 may be fixed at the proximal end. Alternatively, as illustrated in FIGS. 3 and 4 one or more and in the case illustrated all of the cannulae 60, 61, 62 are slidably movable relative to the connectors 20, 21, 22.

Figure 6:
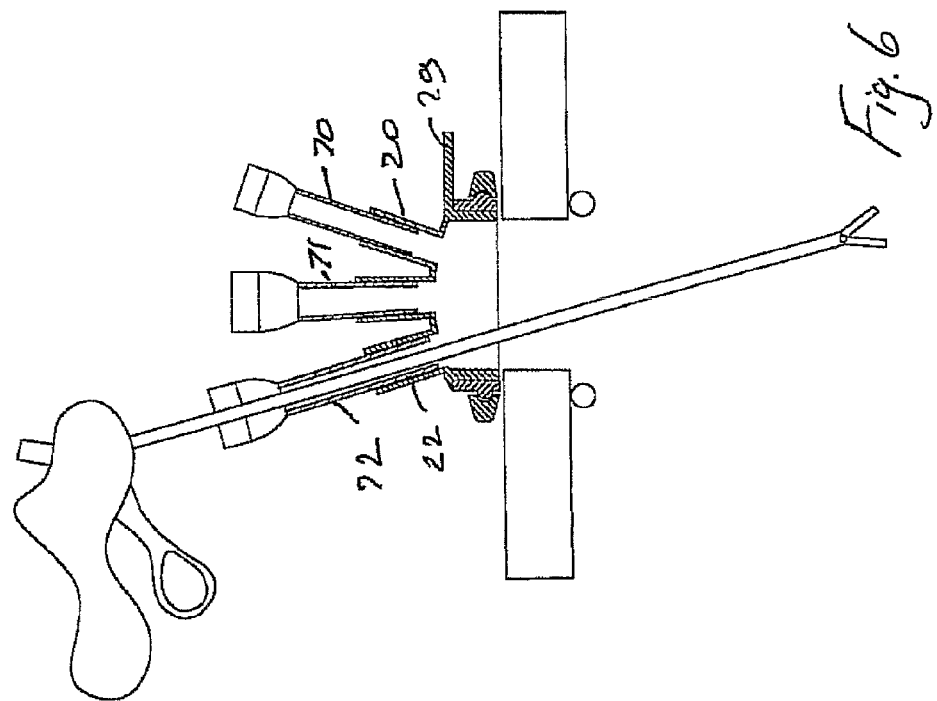
FIG. 6 is a cross sectional view of the device of FIG. 5, in use.
Figure 5:
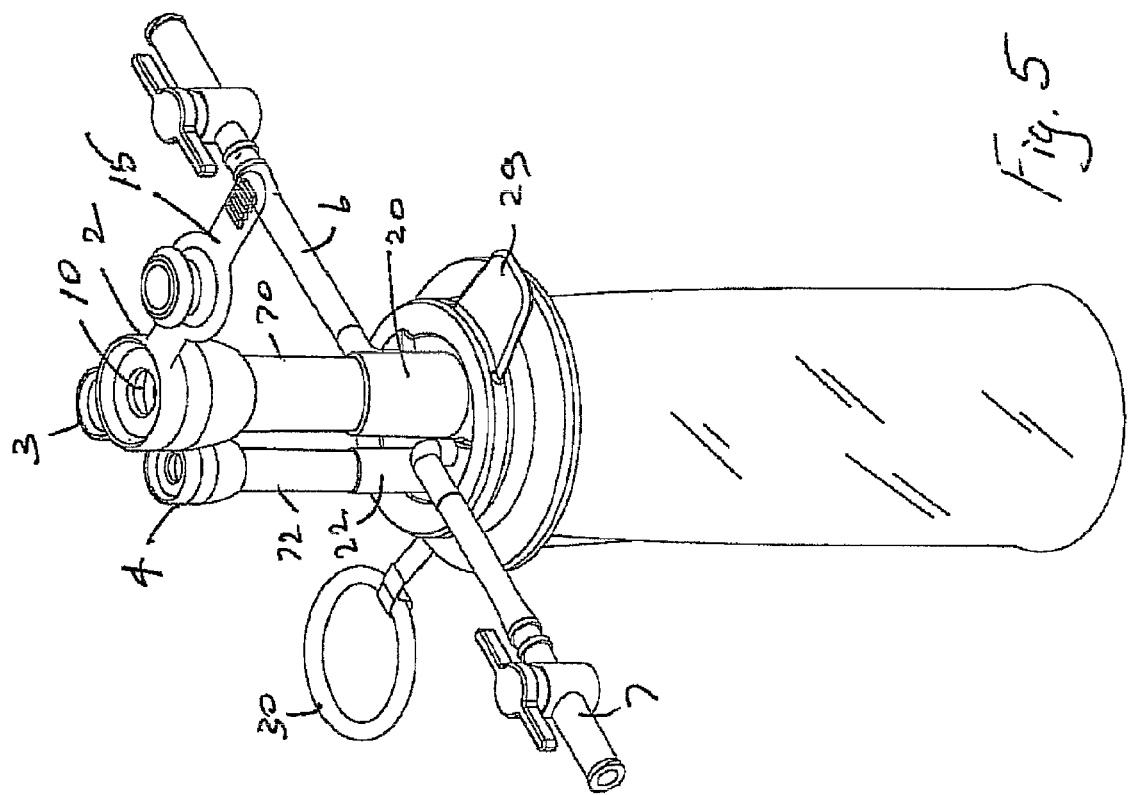
FIG. 5 is an isometric view of another instrument access device of the invention.

Referring now to FIGS. 5 and 6 in this case cannulae 70, 71, 72 extend from the connectors 20, 21, 22 and the proximal seals are provided at the proximal ends of the cannulae 70, 71, 72. One or more of the cannulae 70, 71, 72 may be at least partially flexible. Indeed some or all of the cannulae may be rigid.

Referring especially to FIGS. 7 to 12 a joint between at least one and in this case all of the connectors 20, 21, 22 and the proximal member 25 facilitates movement of the connector(s) relative to the member 25. Referring to FIGS. 7 and 8 in one case the joint comprises a groove 80 or area of reduced thickness to accommodate pivotal or swivelling movement. The arrangement may have an integral bias to return the connector to one position (FIGS. 7, 8(*a*)). FIGS. 10(*a*) and 10(*b*) illustrate a joint 85 which is similar to that of FIGS. 8(*a*) and 8(*b*). Alternatively, the joint may comprise a flexible extension leg 87 to facilitate flexible movement.

Figure 12:
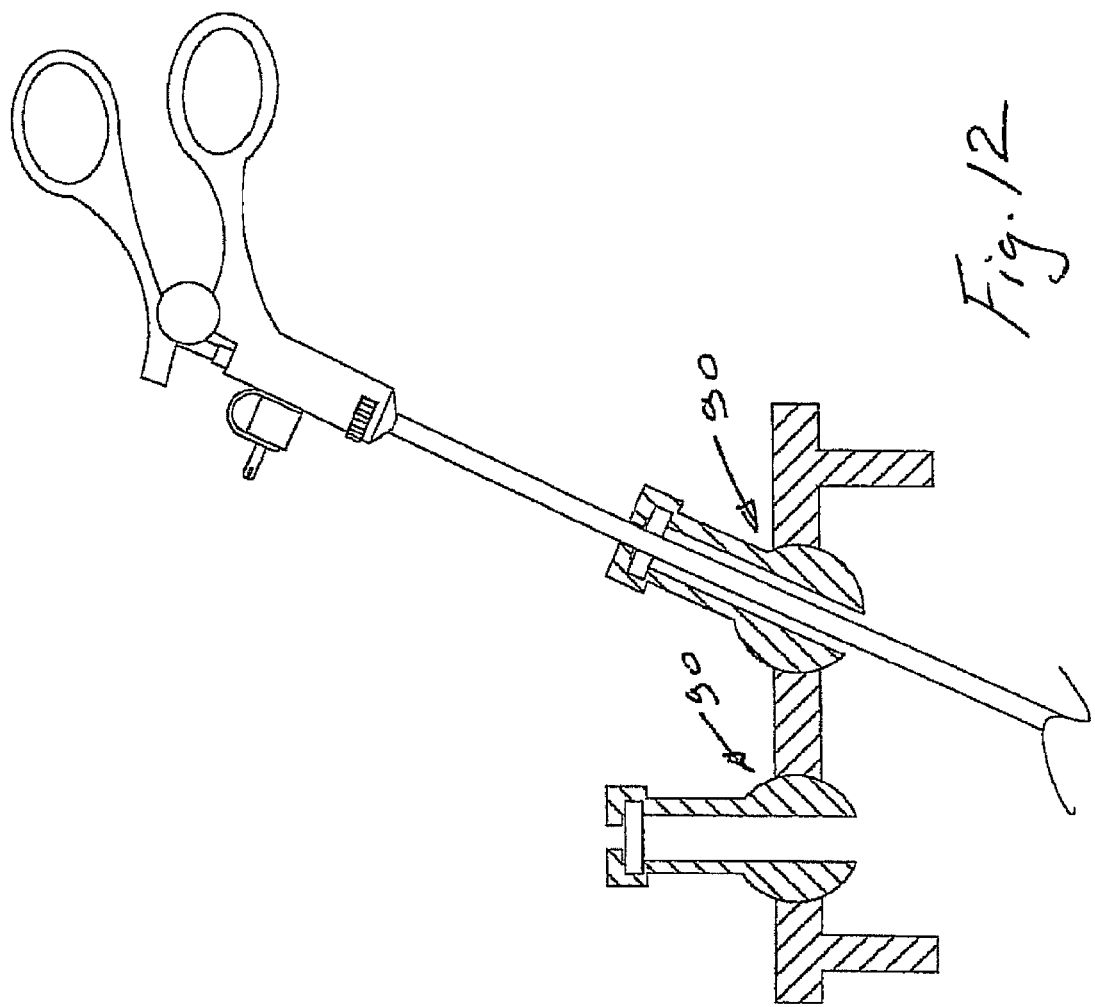
FIG. 12 is a cross sectional view of the device of FIG. 11, in use.
Figure 11:
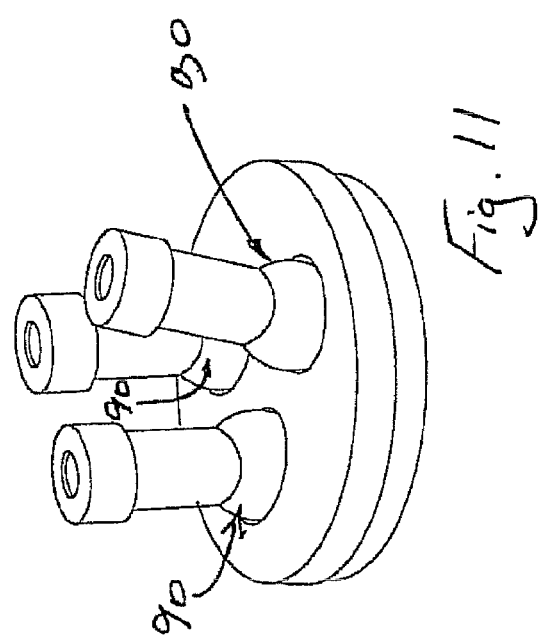
FIG. 11 is an isometric view of another instrument access device of the invention.

Referring to FIGS. 11 and 12 in this case there is a ball and socket type joint 90 between the connector and the proximal member 25 to facilitate movement in many directions.

Figure 13:
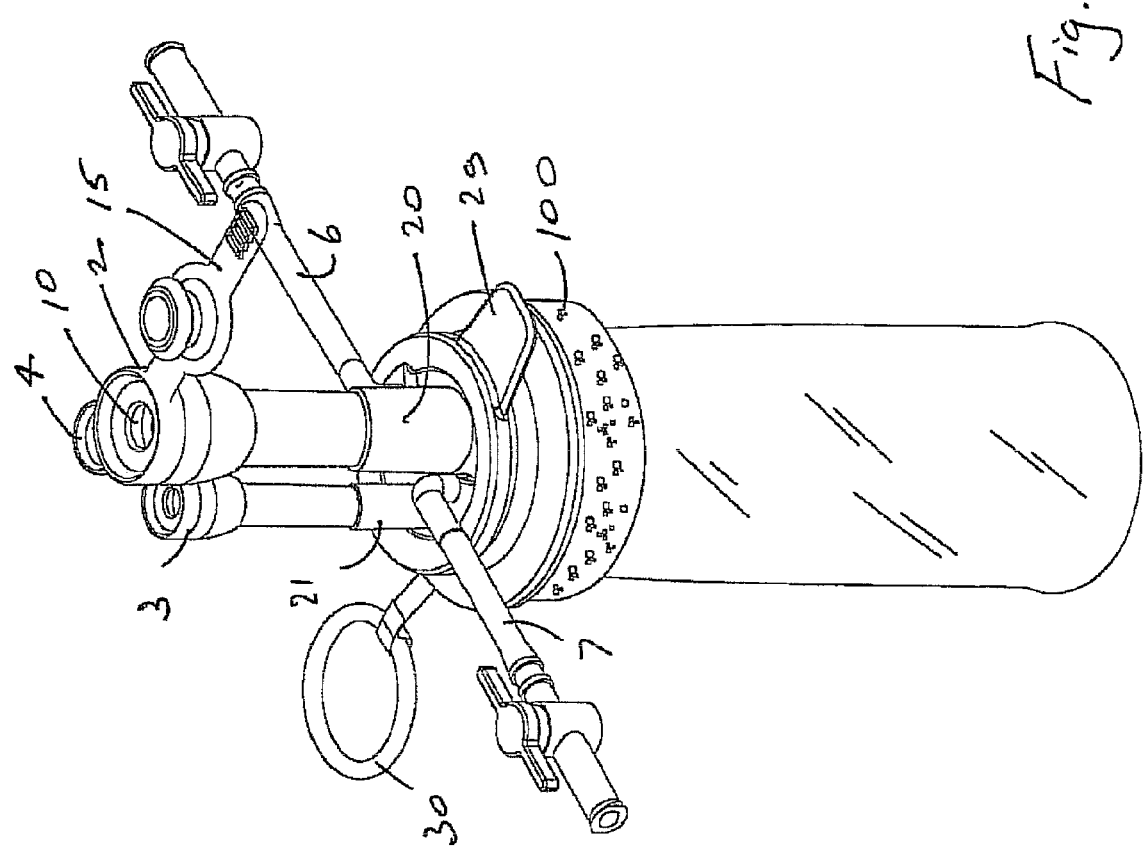
FIG. 13 is an isometric view of another instrument access device according to the invention.
Figure 17:
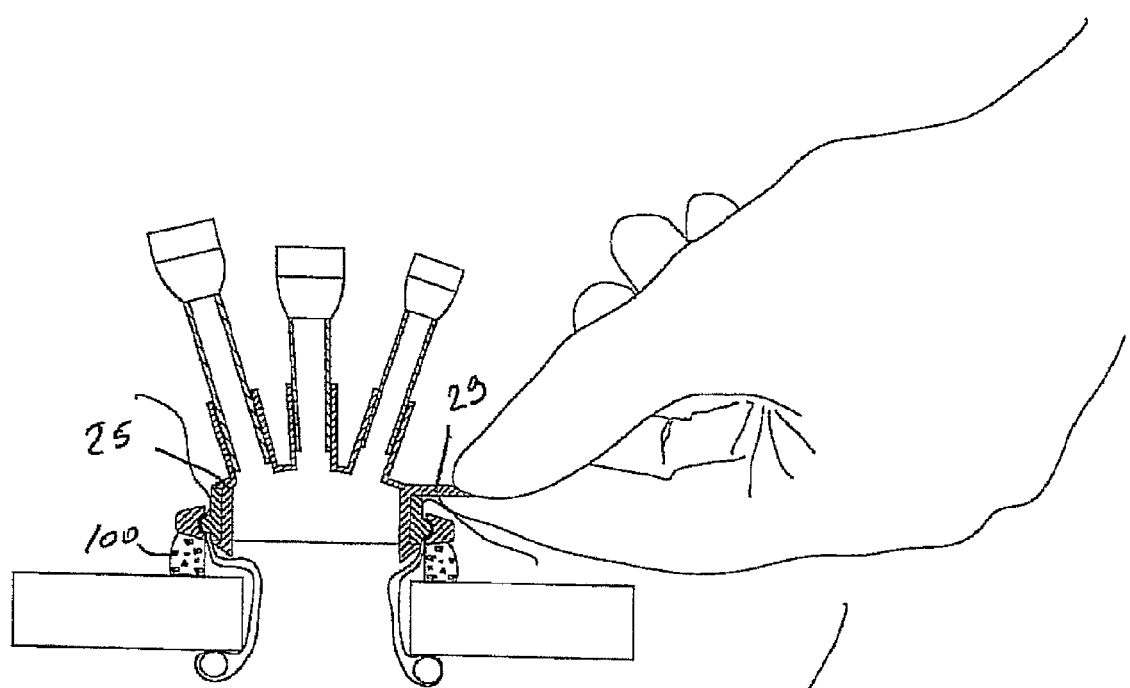

Referring to FIGS. 13 to 15 in one case there is a spacer 100, for example comprising a pad of flexible material such as foam or rubber which is interposed between the proximal ring assembly 26 and the body outside the wound opening. The pad 100 is sufficiently flexible to allow swivelling or pivotal movement of the device in situ to provide even a greater freedom of movement. In addition, because the proximal ring assembly 26 is spaced away from the body the retractor sleeve 27 can be more easily manipulated and does not become trapped at the proximal end. The pad 100 may also assist in reducing trauma and bruising during surgery.

Figure 18:
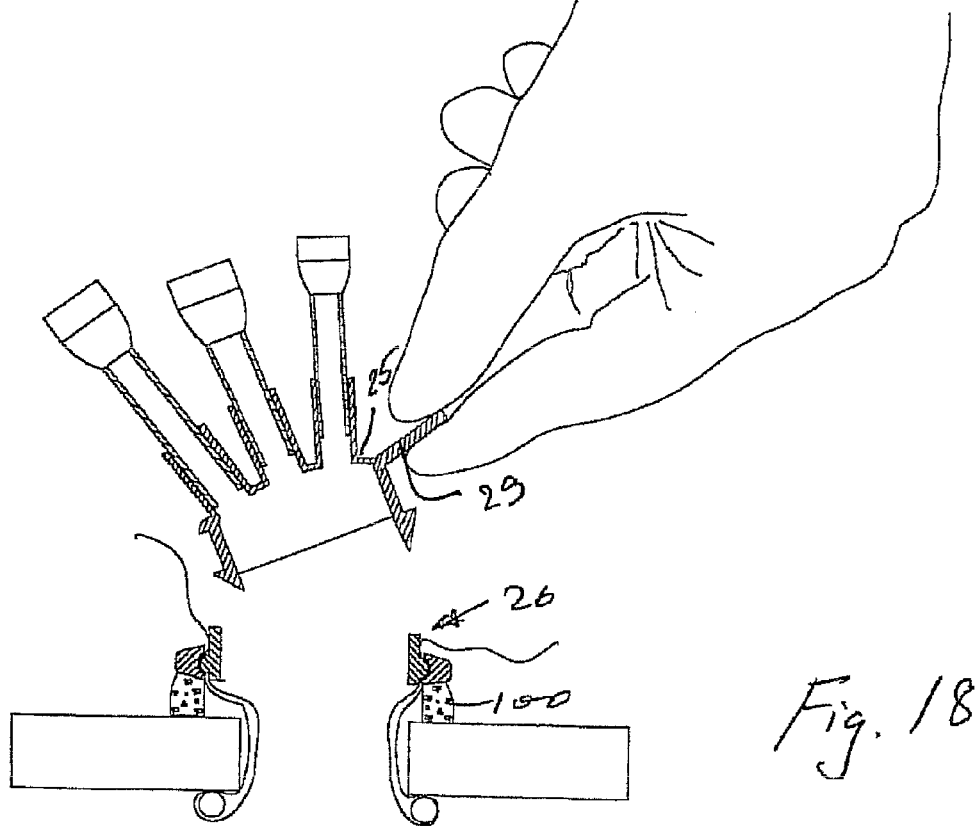

FIGS. 18 and 19 illustrate the use of the tab 29 in demounting the instrument access device from the retractor base, the base 25 being detached from the proximal ring assembly 26.

Referring now to FIGS. 19 to 22 there is illustrated another instrument access device which in this case has a port or hole 110 to facilitate insertion of a small instrument 111 or tube 112. The port 110 has closure cap 113. In this case the port 110 is provided in the proximal member 25. The port has a relatively small diameter, typically 3 to 5 mm and can be used to allow escape of smoke which may be generated during the procedure such as a cauterisation procedure. The tube 112 may have a luer connector 115 at the proximal end which may be attached to a vacuum/suction source. The tube may also be used for blood removal and/or irrigation/cleaning. The port 110 can also be used for desufflation and/or insufflation.

Referring to FIGS. 31 to 35 there is illustrated another instrument access device 200 according to the invention which is similar to the devices described above and like parts are assigned the same reference numerals. In this case the access device comprises a first instrument insertion device 201, a second instrument insertion device 202, a third instrument insertion device 203, and a fourth instrument insertion device 204. The first instrument insertion device 201 can accommodate an instrument of up to 10 mm diameter and has a reducer cap 15 which, when closed, converts the insertion device to accommodate an instrument of up to 5 mm diameter. The second, third and fourth instrument insertion devices 202, 203, 204 can all accommodate instruments of up to 5 mm diameter.

The device 200 of FIGS. 31 to 35 is particularly suitable for use in a method of performing a laproscopic surgical procedure as described in our US2009/0036745A, the entire contents of which are incorporated herein by reference. The three instrument insertion devices 202, 203, 204 extend in a direction towards a surgeon performing the procedure. The pull tab 29 can be used as a reference in this aspect, pointing away from the surgeon. The arrangement of the insertion devices is ergonomically efficient as the surgeon can readily manipulate tissue retraction and camera instruments inserted through the devices 202, 203, 204. The larger device 204 points away from the surgeon as it may be used only occasionally during the procedure, for example in removing dissected tissue. In this way the available space is optimised. One example of a procedure using the device of FIGS. 31 to 35 is a cholecystectomy.

Referring to FIGS. 36 to 40 there is illustrated another instrument access device 250 according to the invention which is similar to the devices described above and like parts are assigned the same reference numerals. In this case the access device comprises first, second and third instrument insertion devices 251, 252, 253 respectively. The first instrument insertion device 251 can accommodate an instrument of up to 10 mm diameter and has a reducer cap 15 which, when closed, can convert to accommodate an instrument of up to 5 mm diameter. The second and third instrument insertion devices 252, 253 can all accommodate instruments of up to 5 mm diameter.

The device 250 of FIGS. 36 to 40 is particularly suitable for use in surgical procedures which require the use of larger diameter instruments such as a morcellator (which is used for example in gynecological procedures such as uterus removal), or instruments for tissue specimen removal, gastric banding, endocath bag delivery (which are used for larger organs such as a kidney. Larger organs/tissue specimens can be removed by detaching the access device from the retractor base.

In the case of the access devices of FIGS. 31 to 40 an incision of typically 10 to 25 mm in length is made. The devices allow procedures to be carried out laparoscopically which would not otherwise be possible through such a small incision.

Referring to FIGS. 41 to 45 there is illustrated another instrument access device 300 according to the invention which is similar to the devices described above and like parts are assigned the same reference numerals. In this case the access device comprises first, second, third, fourth and fifth instrument insertion devices 301, 302, 303, 304, 305 respectively. The first instrument insertion device 301 can accommodate instruments of up to 10 mm diameter. The device 301 has a reducer cap 15 which, when closed, can convert to accommodate an instrument of up to 5 mm diameter. The second instrument insertion device 302 can accommodate instruments of up to 15 mm diameter. The device 302 has a reducer cap 15 which, when closed, can convert to accommodate an instrument of up to 5 mm diameter. The third instrument insertion device 303 can accommodate instruments of up to 12 mm diameter. The device 303 has a reducer cap 15 which, when closed, can convert to accommodate an instrument of up to 5 mm diameter. The fourth and fifth instrument insertion devices 304, 305 can accommodate instruments of up to 5 mm diameter.

The device 300 of FIGS. 41 to 48 is particularly suitable for use in complex procedures which require multiple instruments. One such procedure is Nissen fundiplication which is a surgical procedure used to treat gastroesophageal reflux disease (GERD). In the case of the device of FIGS. 41 to 48 an incision of typically 20 to 60 mm in length is made. The device allows complex procedures to be carried out laproscopically which would not otherwise be possible.

Figure 47:
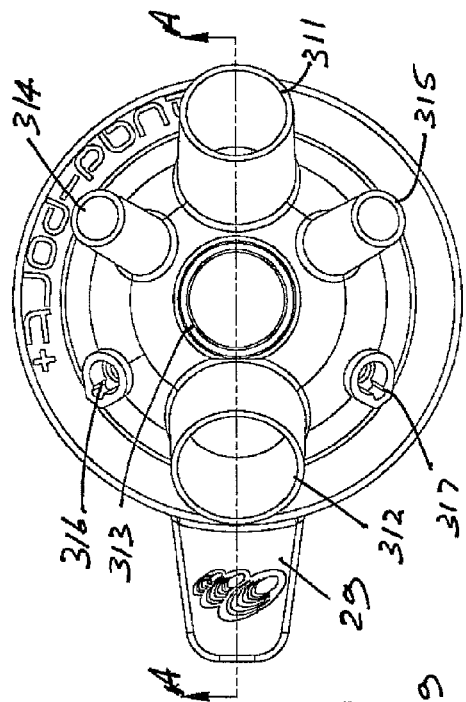
FIG. 47 is a top plan view of the device of FIG. 46.
Figure 48:
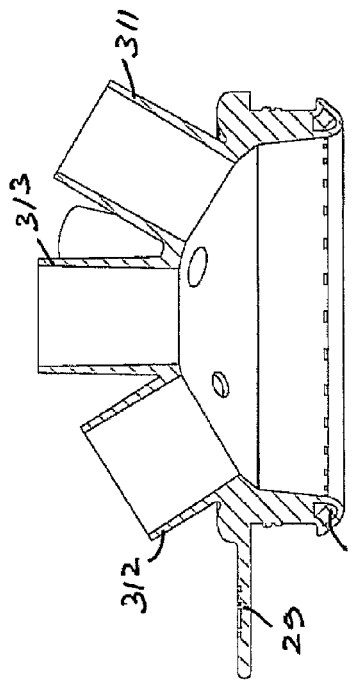
FIG. 48 is a cross sectional view on the line A-A in FIG. 47.
Figure 46:
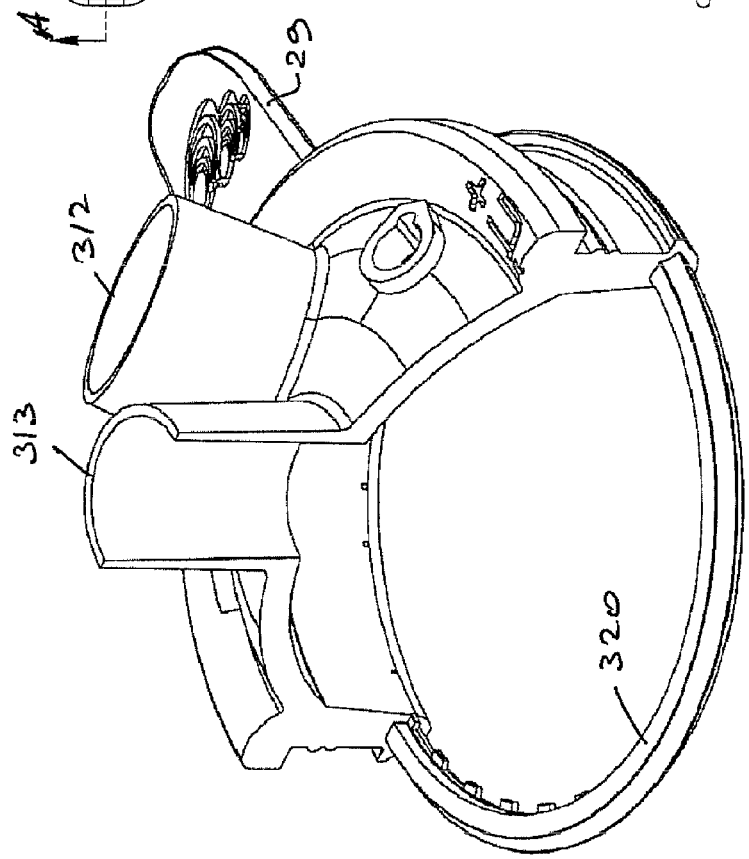
FIG. 46 is an isometric cut-away view of portion of the device of FIGS. 41 to 45.

A base part of the access device of FIGS. 41 to 45 is illustrated in FIGS. 46 to 48. The valves/seals have been omitted in these drawings. The connector or receiver leg parts of the instrument insertion devices 301, 302, 303, 304, 305 are assigned the reference numerals 311, 312, 313, 314, 315 respectively. Access holes 316, 317 for the insufflation/desufflation ports 6, 7 are also illustrated. The base part is of a relatively flexible material and in this case is reinforced by a reinforcing ring 320 of a more rigid material. The reinforcing ring 320 is embedded in the base using overmoulding.

The instrument insertion devices may be coded such as by indicia or colour coding to indicate a particular instrument size that may be used with a particular device size. For example, the colour blue may be used to indicate use with an instrument of up to 5 mm in size, white for up to 10 mm instruments, grey for up to 12 mm instruments, and orange for up to 15 mm instruments.

It will be appreciated that features described with reference to one embodiment of the invention may be utilised with any of the other embodiments.

The invention is not limited to the embodiments hereinbefore described which may be varied in detail.

The invention claimed is:

1. An instrument access device, comprising:
    a wound retractor, including:
        a longitudinal axis,
        a proximal ring-shaped member for location externally of a wound opening,
        a distal ring-shaped member for location within a wound interior, the distal ring-shaped member defining a central opening extending therethrough,
        a sleeve extending at least from the distal ring-shaped member to the proximal ring-shaped member; and
    a seal assembly including a plurality of instrument seals and a plurality of cannulae, wherein:
        each of the instrument seals is located proximal to the proximal ring-shaped member,
        each of the instrument seals is movable with respect to the proximal ring-shaped member, and
        each of the cannulae is coupled to one of the instrument seals and extends distally from the one of the instrument seals into the wound retractor, each of the cannulae is freely movable throughout the central opening of the distal ring-shaped member, and at least one cannula is configured to bend to have a curved configuration and extends distal to the distal ring-shaped member of the wound retractor.

2. The instrument access device of claim 1, wherein the plurality of seals includes three instrument seals, the three instrument seals being bisected by a longitudinally-extending plane through the seal assembly.

3. The instrument access device of claim 1, wherein two instrument seals are substantially equally-spaced from a longitudinally-extending plane.

4. An instrument access device, comprising:
    a wound retractor, including:
        a longitudinal axis,
        a proximal ring-shaped member for location externally of a wound opening,
        a distal ring-shaped member for location within a wound interior,
        a sleeve extending at least from the distal ring-shaped member to the proximal ring-shaped member, and
        a central passage extending through the proximal ring-shaped member, the distal ring-shaped member, and the sleeve; and
    a seal assembly including a plurality of instrument seals, a plurality of connectors, and a plurality of cannulae, wherein:
        each of the instrument seals is located proximal the proximal ring-shaped member,
        each of the instrument seals is movable with respect to the proximal ring-shaped member,
        each of the instrument seals includes a longitudinal axis, with distances between longitudinal axes of the instrument seals increasing in a direction extending proximally from a proximal side of the proximal ring-shaped member,
        each of the instrument seals is supported by one of the connectors, and
        each of the cannulae extends through one of the connectors and the central passage, with at least one connector and at least one cannula being configured to flex between straight and bent configurations.

5. The instrument access device of claim 4, wherein the longitudinal axes of the instrument seals are each angled relative to the longitudinal axis of the wound retractor.

6. The instrument access device of claim 4, wherein the plurality of instrument seals includes three instrument seals, longitudinal axes of the three of the instrument seals being substantially coplanar.

7. The instrument access device of claim 4, wherein each of the instrument seals is coupled to one of the connectors and to one of the cannulae.

8. An instrument access device, comprising:
a wound retractor, including:
   a longitudinal axis,
   a proximal ring-shaped portion for location externally of a wound opening,
   a distal ring-shaped portion for location within a wound interior, and
   a retraction sleeve extending at least proximally from the distal ring-shaped portion to the proximal ring-shaped portion; and
a seal assembly, including:
   at least one instrument seal spaced proximal to the proximal ring-shaped portion and laterally movable with respect to the proximal ring-shaped portion,
   a base member,
   at least one tubular seal connector having a distal end at the base member, the at least one tubular seal connector connecting the at least one instrument seal to the base member, and
   at least one cannula, a proximal end of the at least one cannula being coupled to a distal end of the at least one instrument seal, the at least one cannula extending through the at least one tubular seal connector and distal to the distal end of the at least one tubular seal connector and the base member, the at least one cannula having a passage configured to receive an instrument inserted through the at least one instrument seal.

9. The instrument access device of claim 8, wherein the at least one instrument seal includes a plurality of instrument seals, the at least one tubular seal connector includes a plurality of tubular seal connectors, and the at least one cannula includes a plurality of cannulae.

10. The instrument access device of claim 9, wherein each of the instrument seals is spaced proximal to the proximal ring-shaped portion by one of the tubular seal connectors.

11. The instrument access device of claim 8, wherein the at least one cannula is slidable relative to the at least one tubular seal connector.

12. The instrument access device of claim 8, further including a spacer member coupled to a distal surface of the proximal ring-shaped portion.

13. The instrument access device of claim 12, wherein the spacer member includes a pad made of foam or rubber.

14. The instrument access device of claim 8, wherein the at least one tubular seal is coupled to the proximal ring-shaped portion by the base member.

15. The instrument access device of claim 14, wherein the seal assembly further includes a port configured to provide fluid communication between proximal and distal sides of the base member.

16. The instrument access device of claim 15, wherein the seal assembly further includes a closure cap configured to close the port.

17. The instrument access device of claim 8, wherein the proximal end of the at least one cannula is received within the at least one tubular seal connector.

* * * * *